(12) United States Patent
Kim

(10) Patent No.: US 11,906,514 B2
(45) Date of Patent: Feb. 20, 2024

(54) ASSAY FOR RAPID DETECTION OF CEREBROSPINAL FLUID LEAKS

(71) Applicants: NSPC Technologies, LLC, Rockville Centre, NY (US); Gwangju Institute of Science and Technology, Gwangju (KR)

(72) Inventor: Min-Gon Kim, Gwangju (KR)

(73) Assignees: NSPC Technologies, LLC, Rockville Centre, NY (US); Gwangju Institute of Science and Technology, Gwangju (KR)

(*) Notice: Subject to any disclaimer, the term of this patent is extended or adjusted under 35 U.S.C. 154(b) by 83 days.

(21) Appl. No.: 17/835,238

(22) Filed: Jun. 8, 2022

(65) Prior Publication Data

US 2023/0015102 A1   Jan. 19, 2023

Related U.S. Application Data

(60) Provisional application No. 63/335,920, filed on Apr. 28, 2022, provisional application No. 63/240,180, filed on Sep. 2, 2021, provisional application No. 63/216,884, filed on Jun. 30, 2021.

(51) Int. Cl.
  *G01N 33/543* (2006.01)
  *G01N 33/561* (2006.01)
  *G01N 33/68* (2006.01)

(52) U.S. Cl.
  CPC ..... *G01N 33/54388* (2021.08); *G01N 33/561* (2013.01); *G01N 33/6803* (2013.01); *G01N 2333/42* (2013.01); *G01N 2333/79* (2013.01)

(58) Field of Classification Search
  CPC .......... G01N 33/558; G01N 33/54387; G01N 33/54388; G01N 33/54389; G01N 33/561; G01N 33/6803; G01N 2333/42; G01N 2333/79; B01L 2300/0825
  USPC ....... 422/400, 401, 420, 421, 425, 426, 430; 435/287.9, 970, 805, 810; 436/169, 170, 436/514, 518, 530, 810
  See application file for complete search history.

(56) References Cited

U.S. PATENT DOCUMENTS

2014/0004622 A1   1/2014  Palmer et al.
2022/0091118 A1   3/2022  Kim et al.

FOREIGN PATENT DOCUMENTS

WO   2020-160392 A1   8/2020

OTHER PUBLICATIONS

International Search Report and Written Opinion dated Sep. 7, 2022 issued in PCT International Application No. PCT/US2022/032672.

*Primary Examiner* — Christopher L Chin
*Assistant Examiner* — Christina Lusi
(74) *Attorney, Agent, or Firm* — Amster, Rothstein & Ebenstein LLP

(57) ABSTRACT

The invention encompasses methods and test strips for detecting the presence of cerebrospinal fluid (CSF) in a biological sample with a lateral flow device which uses lectin conjugates, anti-antigen conjugates, an immobilized serum line, and an immobilized anti-antigen line.

20 Claims, 15 Drawing Sheets

Figure 1:
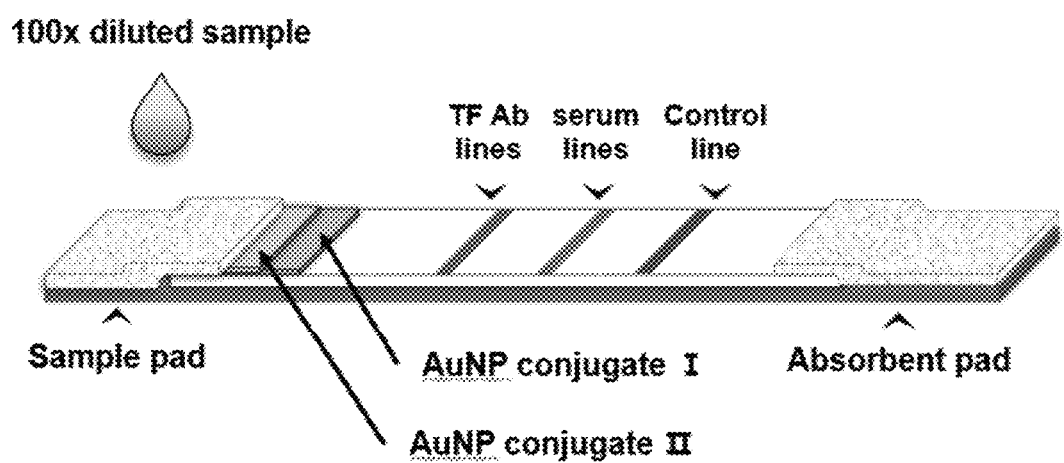

A.

B.

ASSAY FOR RAPID DETECTION OF CEREBROSPINAL FLUID LEAKS

I. CROSS-REFERENCE TO RELATED APPLICATIONS

This application claims benefit of U.S. Provisional Application No. 63/216,884, filed Jun. 30, 2021, and of U.S. Provisional Application No. 63/240,180, filed Sep. 2, 2021, and of U.S. Provisional Application No. 63/335,920 filed Apr. 28, 2022, the contents of each of which are hereby incorporated by reference.

II. BACKGROUND OF THE INVENTION

Spinal fluid leak as a result of incidental durotomy during spinal surgery is a relatively common complication that occurs with an incidence of 2-17% [1-6]. Usually, spinal fluid leaks are recognized at the time of surgery and are successfully repaired. Occasionally, they present in a delayed fashion, for example, if a small durotomy is not recognized at the time of surgery or if the repair is not ideal initially. Spine surgeons are frequently confronted with post-operative fluid collections that may or may not represent a CSF (cerebrospinal fluid) leak. This is more commonly an issue with lumbar spine surgery for degenerative disease. If a patient presents with positional headaches or with clear fluid leakage, then the diagnosis is more easily made. However, in the post-operative period it is sometimes confounding differentiating seromatous fluid from CSF as a patients' symptoms do not always classically present. A patient may present with a bulging subcutaneous collection of fluid whereupon aspiration, the nature of the fluid is not certain. In surgical decision-making, it would be ideal to confirm the diagnosis of CSF leak quickly so that one can initiate repair, which requires surgical intervention particularly if there is skin drainage, which could result in meningitis. It would be advantageous to know if the collection is a seroma as these can often be treated conservatively without return to the operating room. Currently to distinguish CSF from seromatous fluid, one must send out the fluid sample to a laboratory utilizing electrophoresis and obtaining the results can take three to five days.

A combination of protein separation and detection, using electrophoresis and mass spectrometry, has been successfully applied to identify protein biomarkers in CSF [7]. Transferrin (TF) isoforms among protein biomarkers in CSF have been used as a critical diagnostic marker not only for detecting CSF leakage from liquorrhea but also detecting several diseases, including early stage oral cancer [8], chronic alcoholism [9], and diabetic kidney disease [10]. Transferrin (TF) is a glycoprotein (sialo-transferrin) important for maintaining human iron homeostasis. TF is modified to β2TF (asialo-transferrin) in the CSF through the action of brain neuraminidase resulting in the elimination of terminal sialic acid residues on the glycan chains of TF, affording the β2TF glycoform constituting up to 30% of total CSF transferrin. Hence, sensitive and reliable detection of β2TF in non-CSF body fluid samples can point to CSF leakage.

However, although the detection of β2TF has been used in the diagnosis of CSF leakage, there remain several practical limitations in using this method for a point-of-care diagnosis. The minor differences in the TF-based glycan chains make it difficult to distinguish β2TF from sialo transferrin (sTF) since sTF is also a major component in serum, thus sensitivity and specificity are very important. Currently, these TF glycoforms are distinguished using electrophoresis, requiring a relatively long processing time (120-150 min—see, e.g., Carey et al., Journal of The Electrochemical Society, 2020 167:037507) and requires analysis by skilled professionals for diagnosis of CSF leakage. Moreover, an electrophoresis-based assay is usually performed in remote highly specialized professional clinical laboratories that requires additional turnaround time for sample analysis. Thus, conventional electrophoresis for detecting β2TF is not actually suitable as a POC assay for rapid diagnosis and immediate treatment of CSF leakage—which can be critical for patient health.

There remains a need in the art for simple methods and devices for the near real-time rapid detection of CSF leakage which can be readily employed by medical staff during surgical procedures.

III. SUMMARY OF THE INVENTION

Herein disclosed is a novel rapid, sensitive and specific assay for the specific detection of β2TF in fluids, useful in the diagnosis of CSF leakage.

In an embodiment, the lateral flow device comprises a porous substrate. The sample pad, conjugation pad, detection portion and absorbent pad can be disposed on the porous substrate.

A method of detecting the presence of cerebrospinal fluid in a liquid biological sample comprising:
a) distributing the liquid biological sample on to a sample pad of a lateral flow device which comprises, in lateral flow sequence: a sample pad, a conjugate pad, a binding portion, and an absorbent pad, so as to permit the sample to flow along the lateral flow device; and wherein:
  (i) the conjugate pad thereof, downstream in lateral flow from the sample pad, comprises both (A) and (B) thereon, wherein:
    (A) is a first plurality of transferrin-binding antibodies conjugated to a first plurality of nanoparticles, and
    (B) is a plurality of lectin molecules conjugated to a second plurality of nanoparticles;
  (ii) the binding portion thereof, downstream in lateral flow from the conjugate pad, comprises the following separate domains:
    (a) a domain which comprises a second plurality of transferrin-binding antibodies adhered to a surface of the lateral flow device;
    (b) a dried blood serum domain adhered to a surface of the lateral flow device;
b) determining an intensity of an optical signal present at domain (ii)(a) and also at domain (ii)(b);
c) calculating an optical value, wherein the optical value is determined as $=(T1\ \text{intensity})^2 \times (T2\ \text{intensity})$, wherein T1 intensity is the optical signal intensity at domain (ii)(a), and T2 intensity is the optical signal intensity at domain (ii)(b), and determining if the optical value is above or below a pre-determined cut-off value for the lateral flow device, wherein if the optical value is at or above the pre-determined cut-off value for the lateral flow device then the sample contains cerebrospinal fluid, and wherein if the optical value is below the pre-determined cut-off value for the lateral flow device then the sample does not contain cerebrospinal fluid.

A lateral flow device for detecting the presence of cerebrospinal fluid in a liquid biological sample, the device comprising, in sequential order for lateral flow of a liquid, a sample pad; a conjugate pad; a binding portion; and an absorbent pad;

wherein
 a) the sample pad comprises a portion suitable to allow liquid sample flow;
 b) the conjugate pad comprises both (A) and (B),
  wherein (A) comprises first plurality of transferrin-binding antibodies conjugated to a first plurality of nanoparticles, and
  (B) comprises a plurality of lectin molecules conjugated to a second plurality of nanoparticles, which nanoparticles are free to move laterally along the device when a liquid is present thereon;
 c) the binding portion comprises the following separate domains:
  (a) a domain which comprises a second plurality of transferrin-binding antibodies adhered to the surface of the lateral flow device; and
  (b) a dried blood serum domain adhered to the surface of the lateral flow device;

A kit comprising:
 i) a device as recited herein;
 ii) a diluent buffer for a clinical liquid sample from a patient.

A method comprising:
performing surgery on the central nervous system or meninges of a subject;
obtaining one or more samples of the subject's blood or serum or other biological liquid, wherein if more than one sample is obtained then the samples are obtained at different time points during the surgery; and
detecting if cerebrospinal fluid has leaked into the blood or serum or other biological liquid of the subject during surgery comprising the method as recited herein or using the device as recited herein.

A method of diagnosing a subject as having a cerebrospinal fluid leak comprising: detecting if cerebrospinal fluid (CSF) is present in a biological liquid sample from the subject, which is not CSF itself, comprising the method as recited herein or using the device as recited herein, and, where CSF has been detected as present in the sample, diagnosing the subject as having a cerebrospinal fluid leak.

IV. BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1: This figure shows an exemplary lateral flow device for detecting CSF in a fluid. The device is shown in the form of a test strip.

Figure 2:
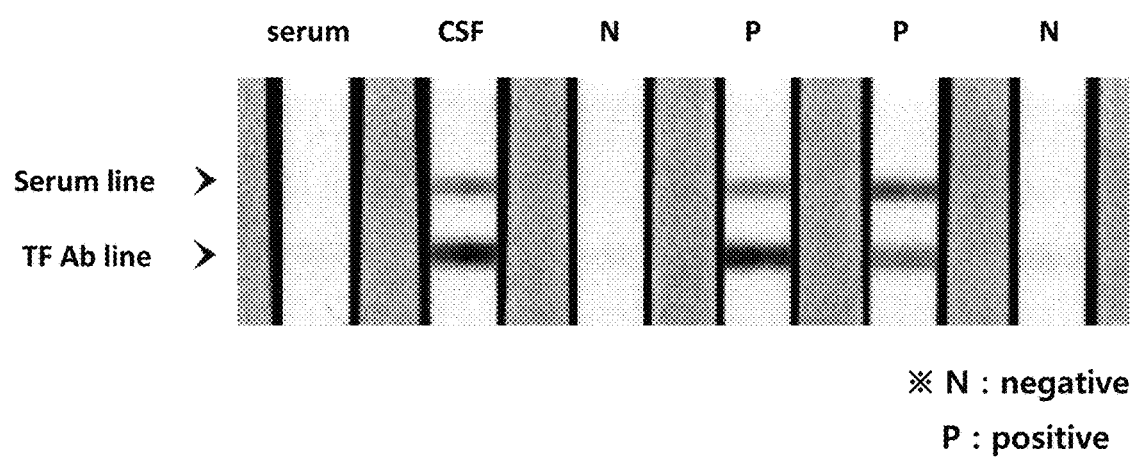

FIG. 2: This figure shows preliminary experiments showing the difference between positive and negative results for the test strip.

Figures 3A, 3B, 3C:
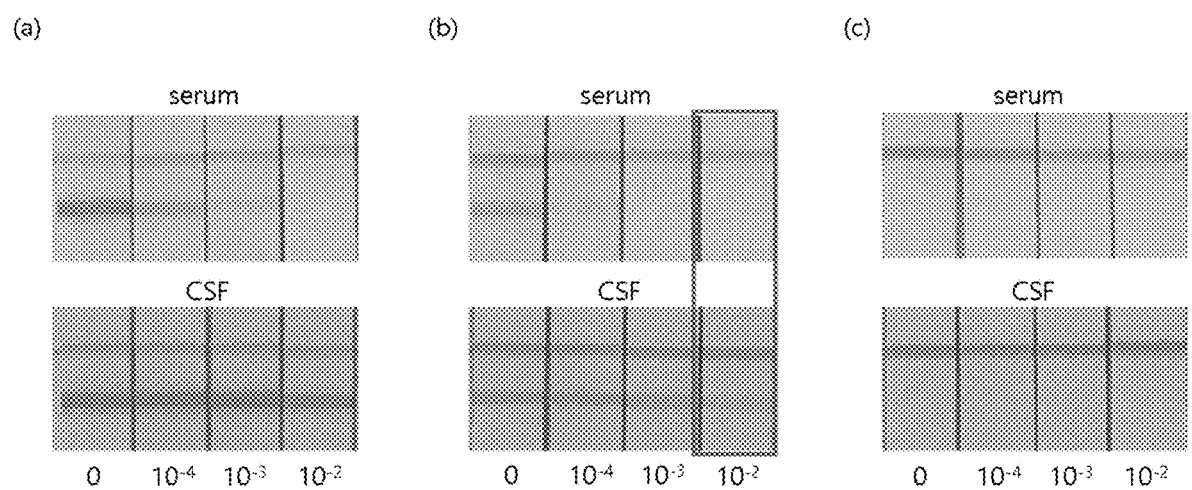

FIG. 3A-3C. Optimized serum concentration as capture molecules and the dilution factor for real world samples: Human serum (H4522, Sigma) was prepared as a (3a) 10-fold dilution; (3b) 100-fold dilution; and (3c) 1000-fold dilution, and was immobilized on the membrane as capture molecules. Serum and CSF sample were also prepared as a 10,000-fold, 1,000-fold, and 100-fold dilution, and the diluted samples were applied to the lateral flow assay strip sensor. The 100-fold diluted human serum as capture molecules and 100-fold diluted serum and CSF samples provided the largest signal differences. 10-fold diluted serum and CSF samples were not tested because the minimum dilution factor to avoid the matrix effect is 100-fold.

Figure 4:
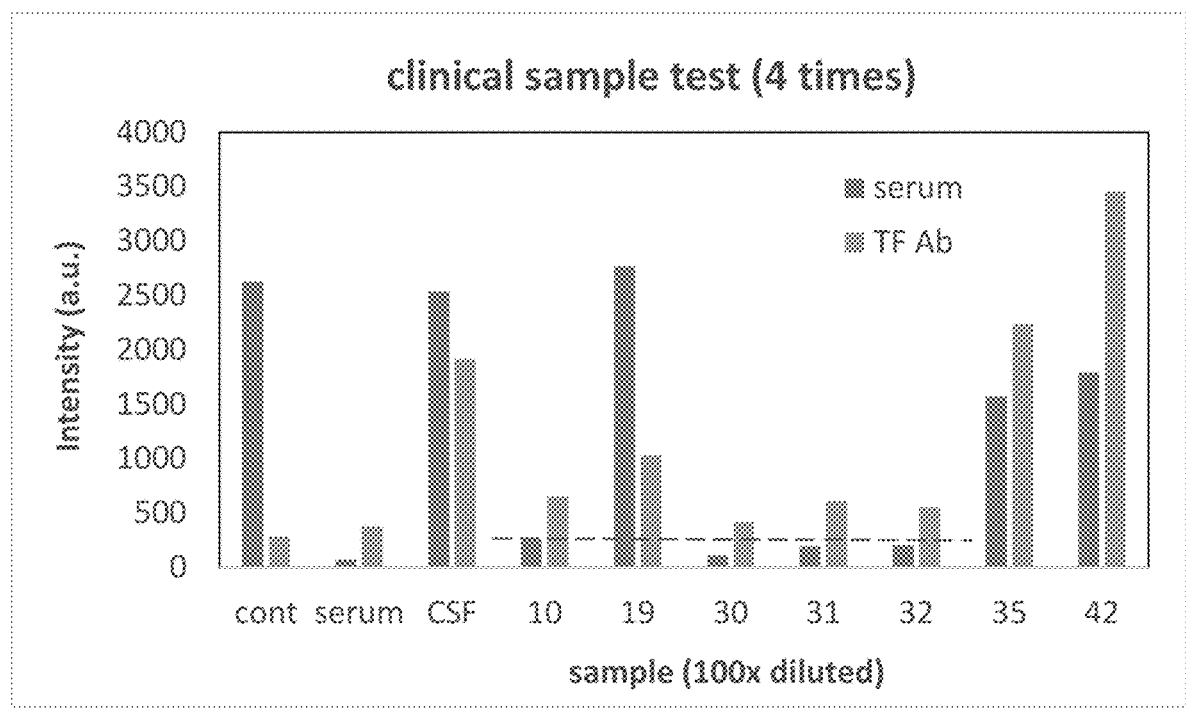

FIG. 4: This figure shows an empirical determination of the required cut off values using clinical samples known to be positive or negative by other methods, as well as control buffer, pure serum and pure CSF. Samples 10, 30, 31 and 32 were negative for CSF. Samples 19, 35 and 42 were positive for CSF. Optical signal cut-off values of above 250 for the serum line and above 600 for the transferrin antibody line were determined to be the accurate distinguishing levels.

Figure 5:
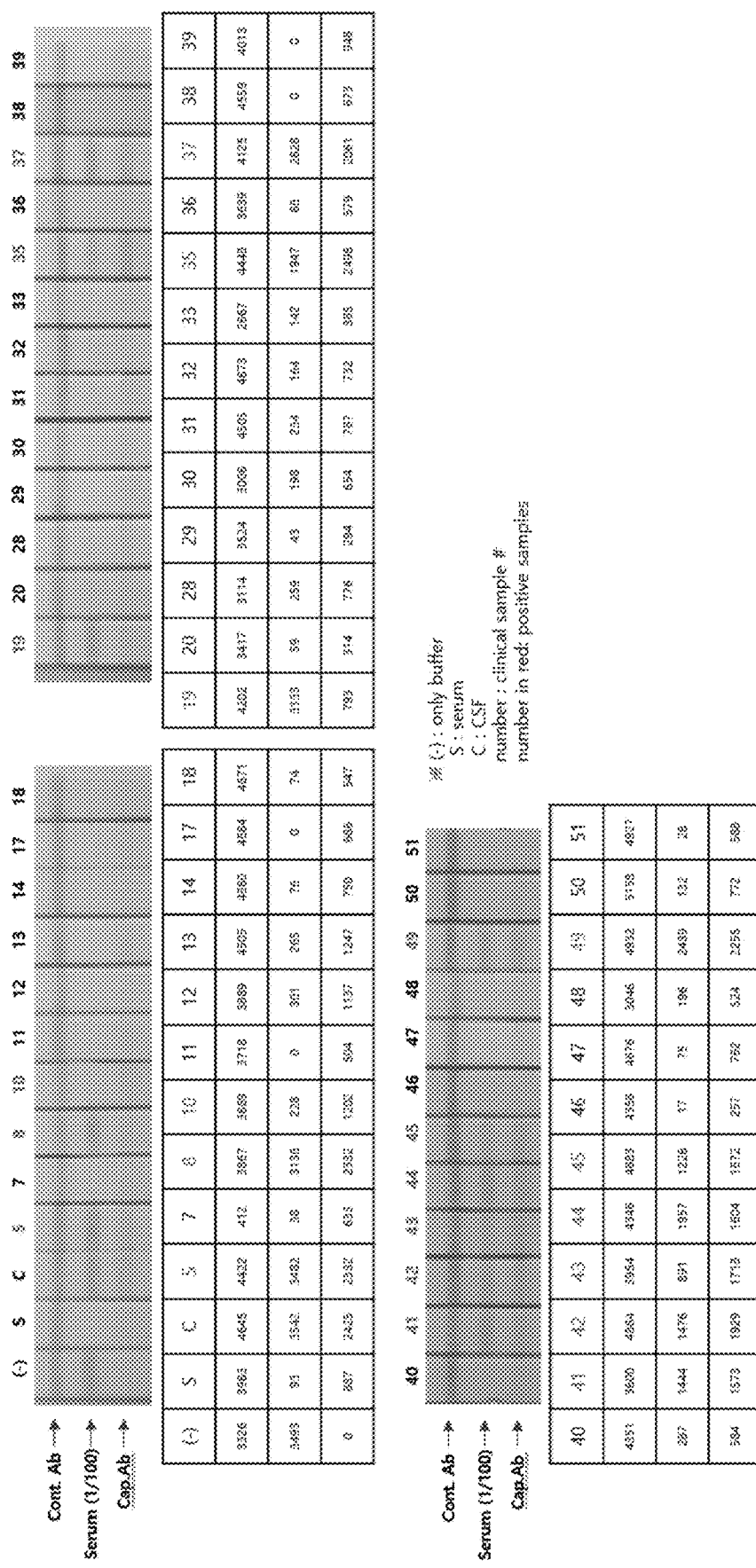

FIG. 5: The results of extensive testing using clinical samples. The control line (Cont. Ab), serum line (Serum) and anti-transferrin antibody signal line (Cap. Ab) are shown. Positive samples visible with the naked eye (and can be confirmed using an optical reader) were #5, 8, 19, 35, 37, 41-45, and 49.

Figure 6:
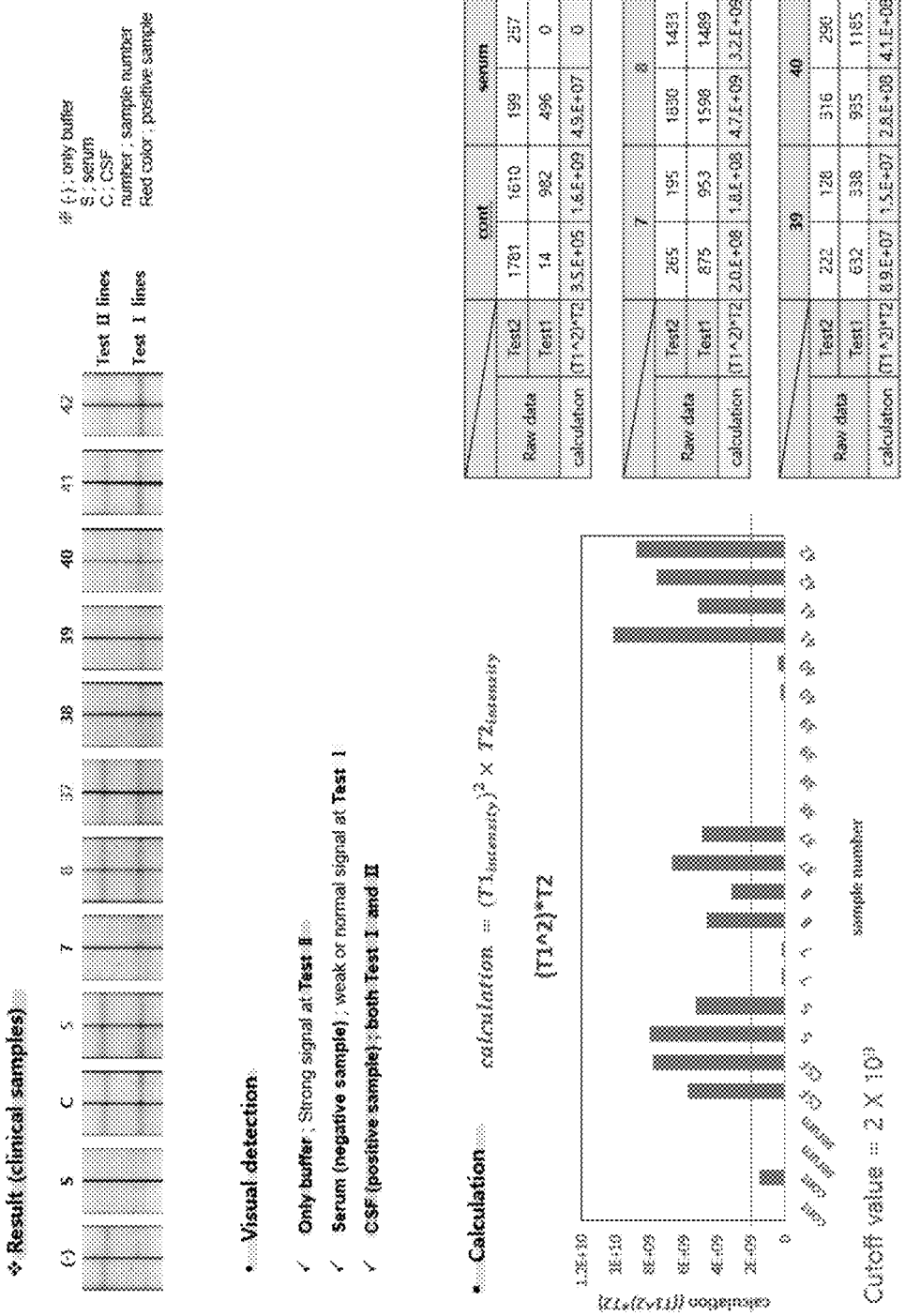

FIG. 6: The results of extensive testing using clinical samples, using a lateral flow device of the disclosure. Positive samples visible with the naked eye (and confirmed using an optical reader) were #5, 8, 37 and 41. 42 also positive, but faint. Cut-off value was empirically determined to be $2\times10^9$. The cut-off value for any test strip system comprising the components described herein can be empirically determined, for example as shown in the figure. The calculation used for the optical value of any sample after it is run is $=(T1\ \text{intensity})^2\times(T2\ \text{intensity})$, where T1 is the transferrin antibody line optical signal value measured and T2 is the serum line optical signal value measured. Preferably, measurement is performed using an optical reader that quantitates the optical signal(s). Where the calculated optical signal value of $(T1\ \text{intensity})^2\times(T2\ \text{intensity})$ for a given sample that has been run on the test strip is in excess of, or at, the pre-determined cut-off value, then the sample is positive for the presence of CSF. Where the calculated optical signal value of $(T1\ \text{intensity})^2\times(T2\ \text{intensity})$ for a given sample that has been run on the test strip is below the pre-determined cut-off value, then the sample is negative for the presence of CSF. The calculated optical signal value of $(T1\ \text{intensity})^2\times(T2\ \text{intensity})$ can be performed by the optical reader, or a calculating device attached thereto, and the optical reader can display, for example a "positive" signal indicating CSF is present in a tested sample, and/or a "negative" signal indicating CSF is absent in a tested sample. When tested against control, serum, CSF and known positive & negative samples, the cut-off between positive and negative biological samples is readily determined. In FIG. 5, cut-off value of $2\times10^9$ is selected as distinguishing between positive samples 5, 8, 37, 41 and 42 versus negative samples 7, 38, 39, and 40.

Figure 7:
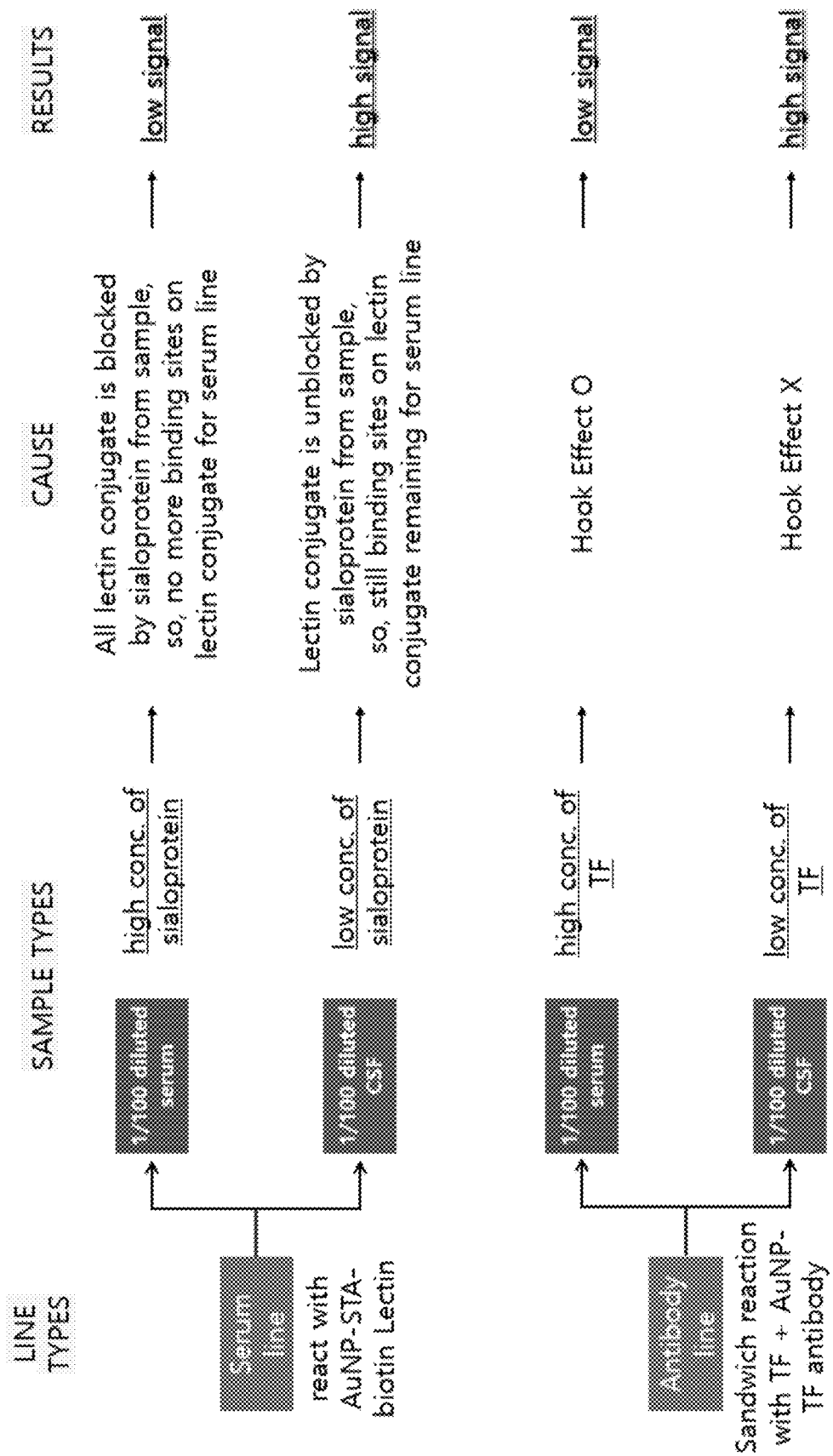
Figures 8A, 8B, 8C, 8D:
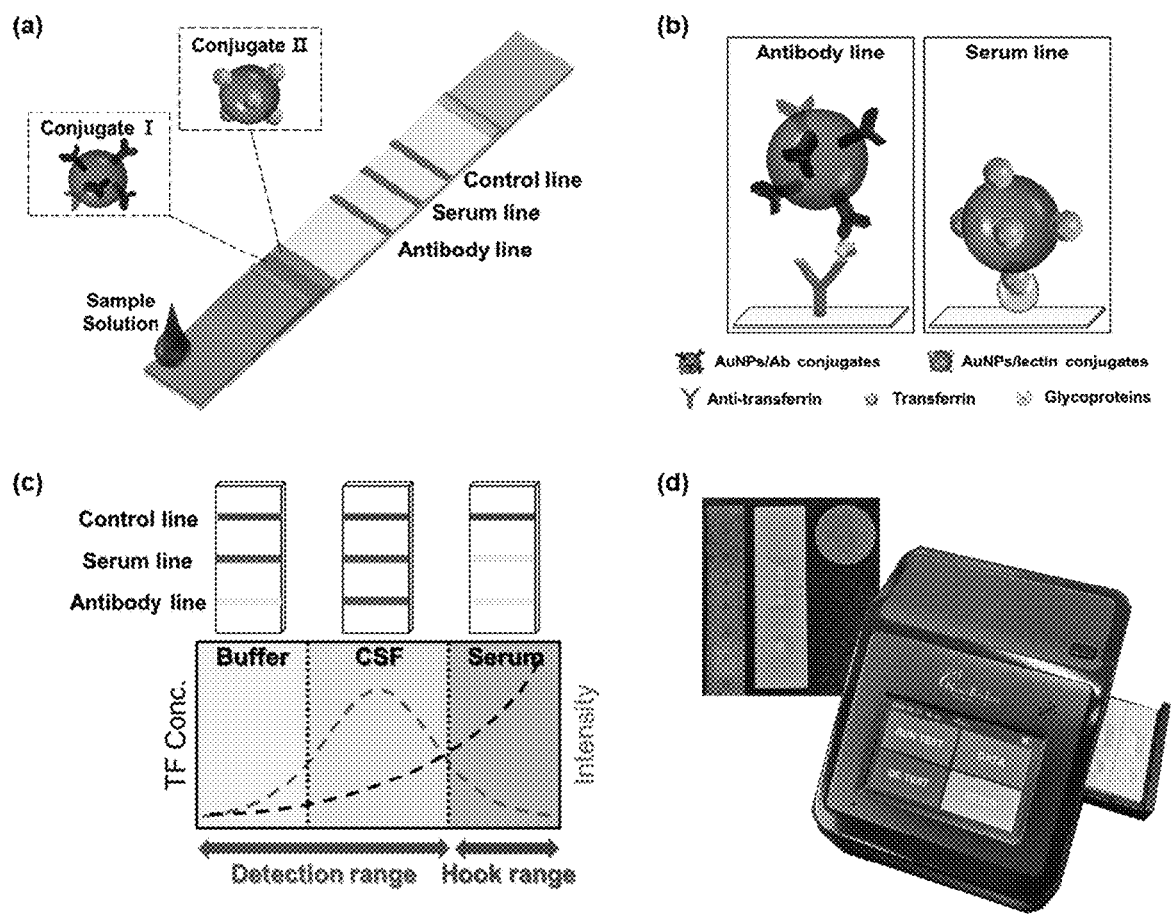

FIG. 7: Schematic representation of line presence or absence for antibody line and serum line using different samples.

FIG. 8A-8D. Schematic illustration of the lateral flow immunoassay (LFI) sensor developed in this work. (a) Two conjugates and two detection lines are used in this platform: Conjugate I (AuNPs/Ab conjugate) and Conjugate II (AuNPs/lectin conjugate); antibody and serum lines are also depicted. (b) Conjugate I captures transferrin (TF) and binds to the immobilized antibody on the membrane enabling a sandwich immunoreaction. Conjugate II binds not only to glycoproteins from the sample, but also glycoproteins from the serum line. (c) An excessive amount of TF from serum causes a hook effect, resulting in no signal. Conjugate I fully reacts with TF, leading to no TF binding on the antibody line. Conjugate II binds to immobilized glycoprotein on the serum line without TF, and this false-positive result is removed by introducing a simple equation for intensity calculation. (d) Images of the developed LFI sensor and the portable detector for point-of-care cerebrospinal fluid leak testing.

FIG. 9A-9D. Determination of correct serum line concentration acting as capture molecules, and also the dilution factor for real samples. Serum at (a) 1000-fold dilution, (b) 100-fold dilution, (c) 10-fold dilution, and (d) undiluted serum are immobilized on the membrane, and each diluted sample with AuNPs/lectin conjugate was applied to the lateral flow immunoassay sensor. C and S stand for control line and serum line, respectively.

FIG. 10A-10D. Determination of correct sample dilution factor with gold nanoparticle (AuNP) conjugate. Anti-transferrin antibody (a, c) without oxidation and (b, d) with oxidation were immobilized on the membrane, and the diluted samples were applied to the lateral flow immunoassay sensor with (a, b) AuNPs/Ab conjugate or (c, d) AuNPs/lectin conjugate. C and A stands for control line and antibody line, respectively.

Figures 11A, 11B, 11C:
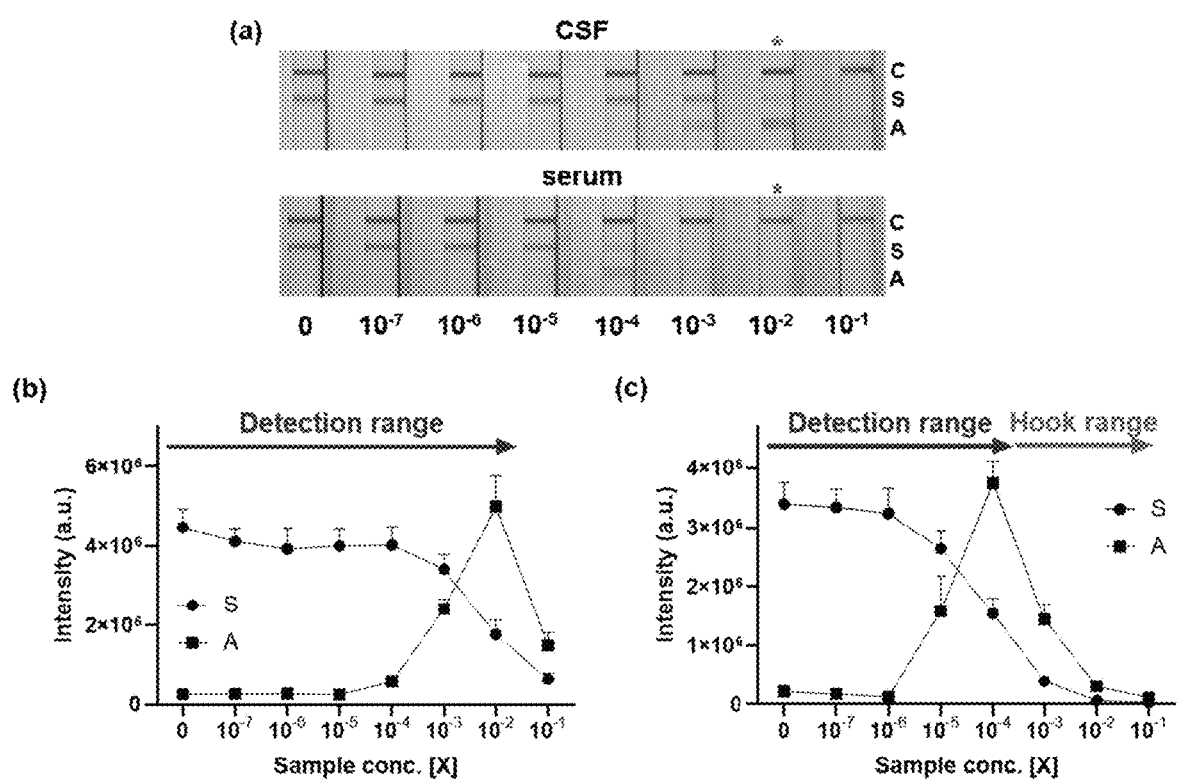

FIG. 11A-11C. Evaluation of the hook effect with cerebrospinal fluid (CSF) and serum under optimized conditions. (a) An image of the lateral flow immunoassay sensor, and the signal intensity of detection lines from (b) the CSF sample and (c) the serum sample. C, S, and A stand for control line, serum line, and antibody line, respectively.

Figures 12A, 12B:
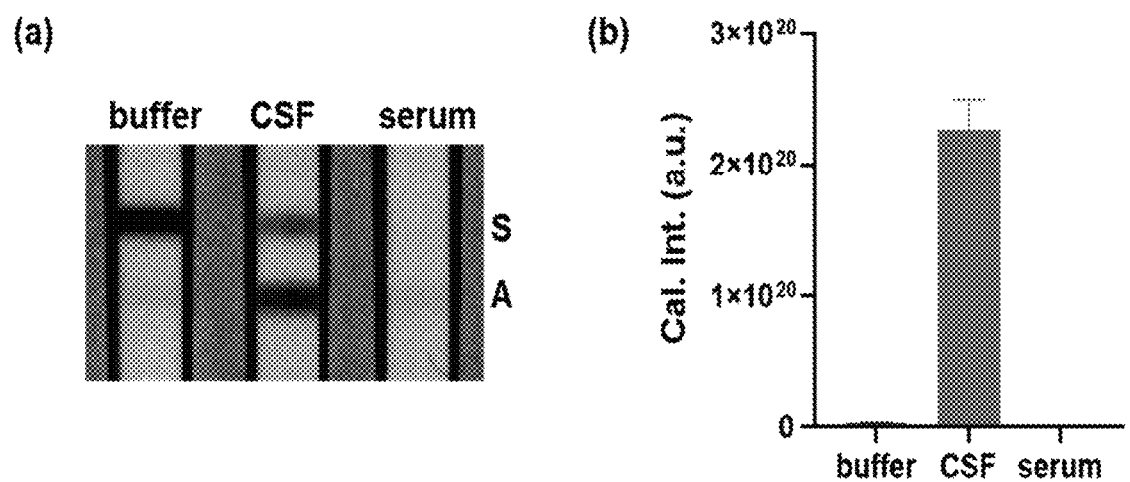

FIG. 12A-12B: Evaluation of the developed lateral flow immunoassay (LFI) sensor with 100-fold diluted buffer, cerebrospinal fluid (CSF) serum samples. (a) An image of the LFI sensor, and (b) the corresponding signal intensity. The signal was calculated by the formula: calculated intensity (a.u.)=(antibody line intensity)$^2$×(serum line intensity). S and A stand for serum line and antibody line, respectively.

Figures 13A, 13B, 13C:
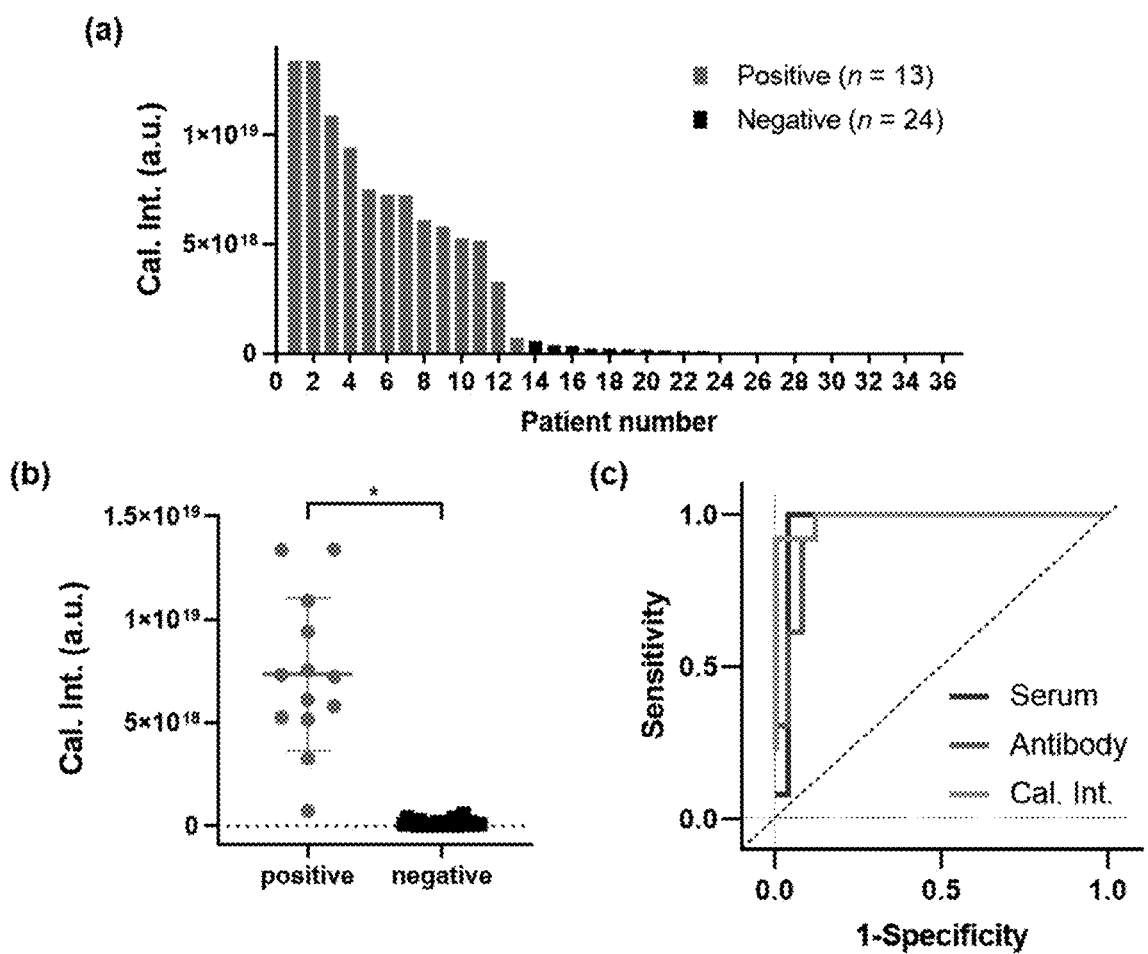

FIG. 13A-13C: Evaluation of the developed lateral flow immunoassay (LFI) sensor with clinical samples (positive n=13, negative n=24, *p<0.001). (a) A waterfall plot of the intensity from the developed LFI sensor. (b) A box plot of the intensity from the developed LFI sensor. (c) Receiver operating characteristic analysis with serum line intensity, antibody line intensity, and calculated intensity.

Figure 14A:
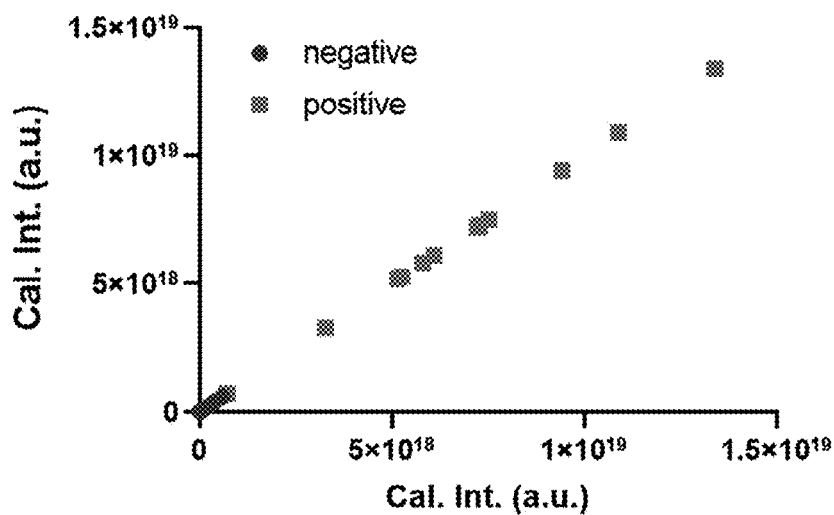
Figure 14B:
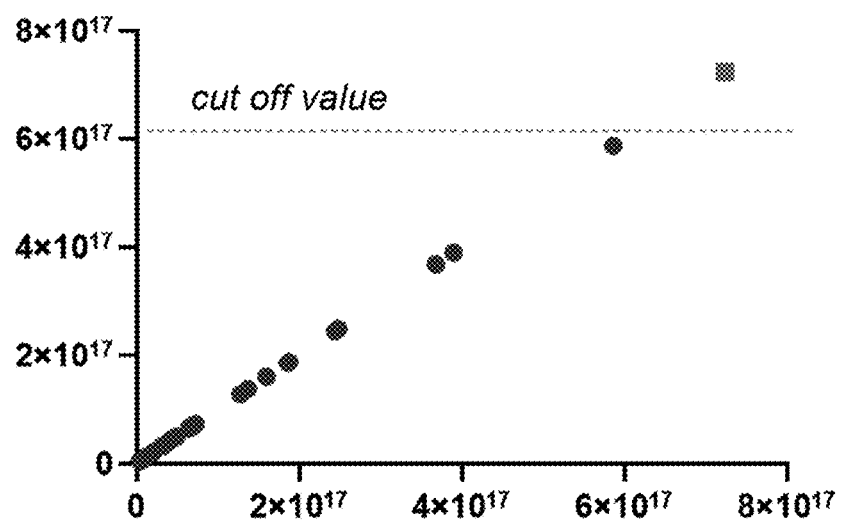

FIG. 14A-14B: (a) ROC curve showing values for negative versus positive results; (b) magnified version of cutoff point (in this case 6.55×10$^{-7}$).

Figure 15:
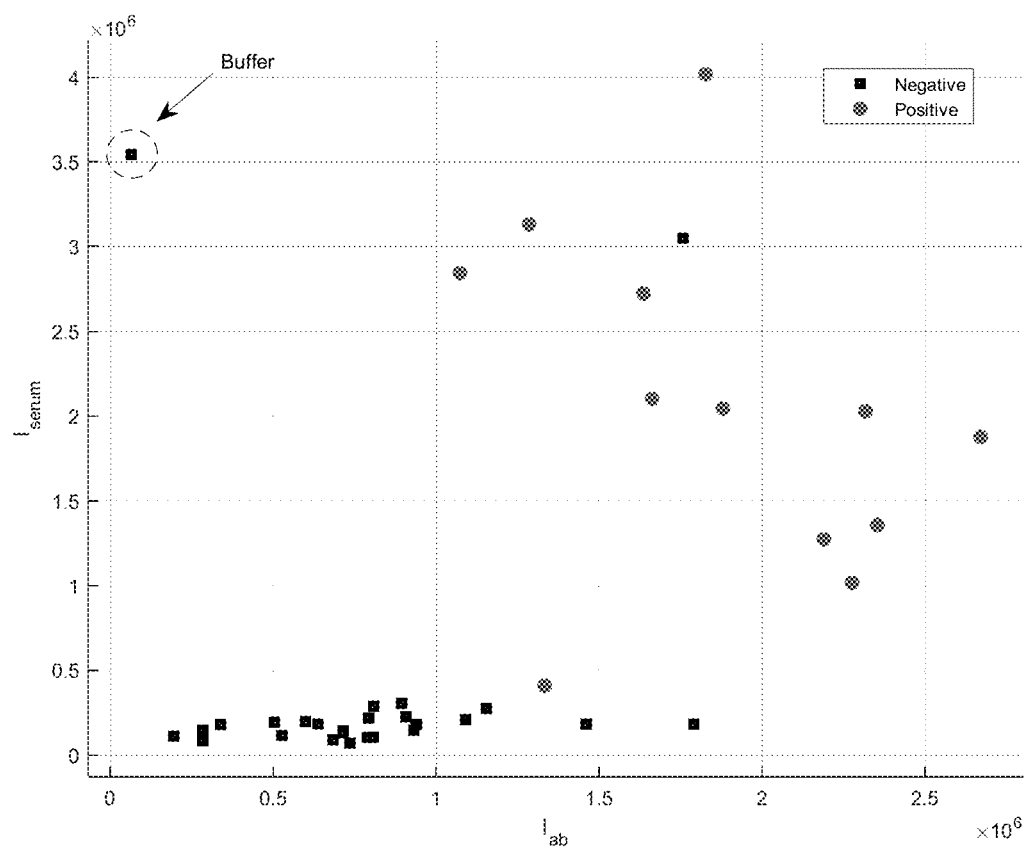

FIG. 15: The LFI sensor data is shown as a scatter plot for Iserum (vertical axis) and Tab (abscissa). The negative samples are shown as black squares and the positive samples as red circles. One negative sample in particular has been labelled as this relates to the buffer response. It is clear from visual inspection that the data separates in to two general regions.

V. DETAILED DESCRIPTION OF THE INVENTION

A method of detecting the presence of cerebrospinal fluid in a liquid biological sample comprising:
a) distributing the liquid biological sample on to a sample pad of a lateral flow device which comprises, in lateral flow sequence: a sample pad, a conjugate pad, a binding portion, and an absorbent pad, so as to permit the sample to flow along the lateral flow device; and wherein:
  (i) the conjugate pad thereof, downstream in lateral flow from the sample pad, comprises both (A) and (B) thereon, wherein:
    (A) is a first plurality of transferrin-binding antibodies conjugated to a first plurality of nanoparticles, and
    (B) is a plurality of lectin molecules conjugated to a second plurality of nanoparticles;
  (ii) the binding portion thereof, downstream in lateral flow from the conjugate pad, comprises the following separate domains:
    (c) a domain which comprises a second plurality of transferrin-binding antibodies adhered to a surface of the lateral flow device;
    (d) a dried blood serum domain adhered to a surface of the lateral flow device;
b) determining an intensity of an optical signal present at domain (ii)(a) and also at domain (ii)(b);
c) calculating an optical value, wherein the optical value is determined as =(T1 intensity)$^2$×(T2 intensity), wherein T1 intensity is the optical signal intensity at domain (ii)(a), and T2 intensity is the optical signal intensity at domain (ii)(b), and determining if the optical value is above or below a pre-determined cut-off value for the lateral flow device,
  wherein if the optical value is at or above the pre-determined cut-off value for the lateral flow device then the sample contains cerebrospinal fluid, and wherein if the optical value is below the pre-determined cut-off value for the lateral flow device then the sample does not contain cerebrospinal fluid.

In embodiments, in the sample pad portion, the first plurality of transferrin-binding antibodies have been oxidized previously to remove sialic acid residues therefrom.

In embodiments, in the binding portion, the second plurality of transferrin-binding antibodies have been oxidized previously to remove sialic acid residues therefrom.

In embodiments, the lectin is a *Sambucus nigra* lectin.

In embodiments, the lectin is biotinylated for attachment to the nanoparticle, and wherein the nanoparticle comprises a streptavidin on its surface.

In embodiments, the optical signals are determined using an optical reader device.

In embodiments, the conjugate pad is comprised of two portions, a first containing thereon the first conjugates (A) and the second containing thereon the second conjugates (B).

In embodiments, (A) and (B) can be present on the same portion of the conjugate pad or on different portions of the conjugate pad. In embodiments, (A) is present prior to (B) in the lateral flow sequence across the conjugate pad. In embodiments, (B) is present prior to (A) in the lateral flow sequence across the conjugate pad.

In embodiments, the optical reader device further provides the optical value calculated in step c).

In embodiments, the dried blood serum domain adhered to the surface of the lateral flow device is human serum.

In embodiments, the liquid biological sample distributed on the sample pad portion has been diluted 90× to 110× with a buffer solution from a raw sample obtained from a human prior to sample being distributed on the sample pad portion.

In embodiments, the buffer solution comprises phosphate buffered saline comprising polyvinylpyrrolidone, a surfactant and is adjusted to pH 7.4

In embodiments, the sample comprise a blood or serum sample obtained from a human.

In embodiments, the sample pad comprises nitrocellulose.

In embodiments, the conjugate pad comprises glass fiber.

In embodiments, the binding portion domain comprises nitrocellulose.

In embodiments, the lectin is attached to the nitrocellulose via a streptavidin-biotin bond. In embodiments, the biotin is attached to the lectin.

In embodiments, the domain which comprises a second plurality of transferrin-binding antibodies adhered to a surface of the lateral flow device is prior in lateral flow sequence to the dried blood serum domain adhered to a surface of the lateral flow device (i.e., "upstream" of the dried blood serum domain). In embodiments, the domain which comprises a second plurality of transferrin-binding antibodies adhered to a surface of the lateral flow device is subsequent in lateral flow sequence to the dried blood serum domain adhered to a surface of the lateral flow device (i.e., "downstream" of the dried blood serum domain).

In embodiments, in the binding portion, the second plurality of transferrin-binding antibodies are immobilized to the nitrocellulose of the binding portion.

In embodiments, the nanoparticles are gold nanoparticles.

In embodiments, predetermined cutoff value for the serum a dried blood serum domain has been determined beforehand to account for Hook effect on binding of human serum glycoproteins to the dried blood serum domain and provide a positive signal.

In embodiments, the predetermined cutoff value has been determined beforehand such that human serum diluted 90× to 110× with a buffer solution from a previously-undiluted serum sample obtained from a human, wherein the sample is not diluted with cerebrospinal fluid and does not contain cerebrospinal fluid, gives an optical value below the predetermined cutoff value.

In embodiments, the predetermined cutoff value has been determined beforehand such that human serum diluted 90× to 110× with a buffer solution from a previously-undiluted serum sample obtained from a human, wherein the sample is diluted with cerebrospinal fluid and does contain cerebrospinal fluid, gives an optical value below the predetermined cutoff value.

In embodiments, the conjugate pad comprises a substrate and wherein neither the first plurality of transferrin-binding antibodies conjugated to a first plurality of nanoparticles nor the plurality of lectin molecules conjugated to a second plurality of nanoparticles are conjugated to the substrate.

In embodiments, each of the domains of the binding portion are in the form of lines which are transverse to a long axis of the lateral flow device.

In embodiments, the lines are 1 to 3 mm wide.

In embodiments, the lines are separated from an adjacent line by 2.5 mm to 3.5 mm.

In embodiments, no lectins are adhered or bound to the surface of the lateral flow device prior to the sample flowing laterally along the device.

In embodiments, the optical signals are directly observed optically a naked eye. In embodiments, a positive antibody line and a positive serum line (corresponding to domains (ii)(c) and (ii)(d), respectively) indicate that CSF is present in the sample. In embodiments, only a single one of a positive antibody line or a positive serum line (corresponding to domains (ii)(c) and (ii)(d), respectively) indicate that CSF is not present in the sample.

In embodiments, the optical signals are directly observed optically using an optical reader device.

In embodiments, the device optionally includes a control domain, downstream of domain (ii)(a) and (ii)(b) which comprises an immunoglobulin adhered to a surface of the lateral flow device.

In embodiments, the immunoglobulin adhered to a surface of the lateral flow device comprises an immunoglobulin G.

In embodiments, the methods further comprise empirically determining the predetermined cutoff value beforehand by running a plurality of samples on the lateral flow device of human serum diluted 90× to 110× with a buffer solution from a previously-undiluted serum sample previously obtained from one or more humans, wherein the serum samples do not contain CSF, and calculating the optical value for each of those plurality from (T1 intensity)×(T2 intensity) as set forth herein, and selecting an optical value which is in excess of every one of the calculated optical values for each of the plurality as the predetermined cutoff value.

In embodiments, the methods further comprise empirically determining the predetermined cutoff value beforehand by (a) running a plurality of samples on the lateral flow device of human serum diluted 90× to 110× with a buffer solution from a previously-undiluted serum sample previously obtained from one or more humans, wherein the serum samples do not contain CSF, and calculating the optical value for each of those plurality from (T1 intensity)×(T2 intensity) as set forth in claim 1, and (b) running a plurality of samples on the lateral flow device of human serum diluted 90× to 110× with a buffer solution from a previously-undiluted serum sample previously obtained from one or more humans, wherein the serum samples do contain CSF, and calculating the optical value for each of those plurality from (T1 intensity)$^2$× (T2 intensity) as set forth in claim 1, wherein steps (a) and (b) can be performed in any order, and (c) selecting an optical value, as the predetermined cut off, which optical value is (i) in excess of every one of the calculated optical values for each of the plurality of samples in step (a) which do not contain CSF, and (ii) is below every one of the calculated optical values for each of the plurality of samples in step (b) which do contain CSF, so as to determine the predetermined cutoff value. In embodiments, human serum in a 100× dilution is employed.

In embodiments, the cutoff value is $6.55 \times 10^{17}$.

In embodiments, the method is completed within 30 minutes of obtaining the sample from the subject. In embodiments, the method is completed within 20 minutes of obtaining the sample from the subject. In embodiments, the method is completed within 15 minutes of obtaining the sample from the subject. In embodiments, the method is completed within 10 minutes of obtaining the sample from the subject.

A method of detecting the presence of cerebrospinal fluid in a liquid biological sample comprising:
a) distributing the liquid biological sample on to a sample pad of a lateral flow device which comprises, in lateral flow sequence: a sample pad, a conjugate pad, a binding portion, and an absorbent pad, so as to permit the sample to flow along the lateral flow device; and wherein:
(i) the conjugate pad thereof, downstream in lateral flow from the sample pad, comprises both (A) and (B) thereon, wherein:
  (A) is a first plurality of transferrin-binding antibodies conjugated to a first plurality of nanoparticles, and
  (B) is a plurality of lectin molecules conjugated to a second plurality of nanoparticles;
(ii) the binding portion thereof, downstream in lateral flow from the conjugate pad, comprises the following separate domains:
  a. a domain which comprises a second plurality of transferrin-binding antibodies which are adhered to a surface of the lateral flow device;
  b. a dried blood serum domain adhered to a surface of the lateral flow device;
b) optically viewing the intensity of an optical signal present at domain (ii)(a) and also at domain (ii)(b);

c) identifying the sample as containing cerebrospinal fluid when both the optical signal at domain (ii)(a) and also at domain (ii)(b) are observable or identifying the sample as not containing cerebrospinal fluid when only one of, or neither of, the optical signal at domain (ii)(a) and t domain (ii)(b) are observable. In embodiments, the optical viewing/observing is done with the naked eye.

A lateral flow device for detecting the presence of cerebrospinal fluid in a liquid biological sample, the device comprising, in sequential order for lateral flow of a liquid, a sample pad; a conjugate pad; a binding portion; and an absorbent pad;
wherein
a) the sample pad comprises a portion suitable to allow liquid sample flow;
b) the conjugate pad comprises both (A) and (B),
wherein (A) comprises first plurality of transferrin-binding antibodies conjugated to a first plurality of nanoparticles, and
(B) comprises a plurality of lectin molecules conjugated to a second plurality of nanoparticles, which nanoparticles are free to move laterally along the device when a liquid is present thereon;
c) the binding portion comprises the following separate domains:
i. a domain which comprises a second plurality of transferrin-binding antibodies adhered to the surface of the lateral flow device; and
ii. a dried blood serum domain adhered to the surface of the lateral flow device.

In embodiments, each of the domains of the binding portion are in the form of lines which are transverse to a long axis of the lateral flow device.

In embodiments, the lines are 1 to 3 mm wide.

In embodiments, the lines are separated from an adjacent line by 2.5 mm to 3.5 mm.

In embodiments, no lectins are bonded to the surface of the lateral flow device.

In embodiments, in the binding, the second plurality of transferrin-binding antibodies have been oxidized previously to remove sialic acid residues therefrom or the second plurality of beta trace protein-binding antibodies have been oxidized previously to remove sialic acid residues therefrom.

In embodiments, the lectin is a *Sambucus nigra* lectin.

In embodiments, the lectin is attached to nanoparticles via streptavidin-biotin interaction.

In embodiments, the lateral flow device further comprises a control domain downstream of the binding portion and upstream of the absorbent pad.

In embodiments, the control domain comprises an immunoglobulin G.

In embodiments, the control domain comprises an anti-mouse immunoglobulin G.

In embodiments, the dried blood serum domain adhered to the surface of the lateral flow device is human serum.

In embodiments, the nanoparticles are gold nanoparticles.

A kit comprising:
i) a device as recited herein;
ii) a diluent buffer for a clinical liquid sample from a patient.

A method comprising:
performing surgery on the central nervous system or meninges of a subject;
obtaining one or more samples of the subject's blood or serum or other biological liquid, wherein if more than one sample is obtained then the samples are obtained at different time points during the surgery; and
detecting if cerebrospinal fluid has leaked into the blood or serum or other biological liquid of the subject during surgery comprising the method as recited herein or using the device as recited herein.

In embodiments, the sample is a serum sample, an otorrhea sample, a rhinorrhea sample, or comprises drainage from a spinal suture area.

A method of diagnosing a subject as having a cerebrospinal fluid leak comprising: detecting if cerebrospinal fluid (CSF) is present in a biological liquid sample from the subject, which is not CSF itself, comprising the method as recited herein or using the device as recited herein, and, where CSF has been detected as present in the sample, diagnosing the subject as having a cerebrospinal fluid leak.

In embodiments, the method further comprises obtaining the sample from the subject. In embodiments, the biological liquid sample is a blood sample, a serum sample, an otorrhea sample, a rhinorrhea sample, or comprises drainage from a spinal suture area.

Results I

Current anti-transferrin antibodies cannot distinguish asialo-transferrin and sialylated-transferrin, and will bind to both. The level of asialo-transferrin in CSF is low, and when diluted into the blood, which contains a relatively large amount of sialated-transferrin is even lower. Thus, simply detecting asialo-transferrin in a sample of post-surgical fluid from a patient, even if one has removed a large proportion, if not all, of the sialated-transferrin can still lead to a very low detection level, especially if the leak is small. This can cause false negatives. A fundamental problem exists when detecting only asialo-transferrin in that antibodies cannot distinguish between asialo- and sialylated transferrin, that the serum ac contains both type (though the large majority is always sialylated) and removal of sialylated transferrins is imperfect. In addition, given the adverse consequences of CSF leaks into the blood due to surgery, it is highly preferable to have a rapid test which can quickly show whether CSF is present in the blood. The present invention provides methods and devices for rapid detection of CSF is present in the blood with high accuracy.

In embodiments of the methods and devices employing a serum line, a pure serum sample (i.e., not diluted with any cerebrospinal fluid) gives a very weak or negative (below cutoff) signal antibody line. In embodiments of the methods and devices employing a serum line, a diluted serum sample (i.e., diluted with an amount of cerebrospinal fluid) gives a positive signal antibody line (i.e., at or above cutoff). The Hook effect plays a role: because a high concentration of transferrin (mainly sialated) exist in the serum, anti-transferrin antibodies of the conjugates and lectin of the nanoparticle conjugates are fully-reacted with the transferrin. In consequence, there are no binding sites left for the anti-transferrin antibodies of the signal line in the binding domain, and the fully bound sample flows past, leaving no signal line, i.e., no binding to the anti-transferrin antibody immobilized on the strip. In contrast, where the serum has been diluted with CSF (which largely contains only asialo-transferrin, and at a lower concentration than sialated-transferrin exists in undiluted serum) there is overall less transferrin per unit volume of the sample as compared to pure serum, which does not cause the Hook effect, and permits binding of the transferrin-bound to the nanoparticles conjugate to the immobilized antibodies of the signal line in the binding portion. The concentration of serum was optimized as a capture molecules in view of the Hook Effect for serum samples and not to cause a Hook Effect for CSF samples (FIG. 3). By weighting the antibody line signal value (T1) as described in FIG. 5 and the descripting thereof, the inventors were finally able to achieve a reproducible and accurate detection for CSF in human serum samples obtained under clinical conditions of neurosurgery and overcome effects of low signal intensity and the Hook effect so as to determine the presence or not of actual human CSF leakage into serum.

It is preferable that the sample obtained from the patient, e.g. a serum, or blood/serum mixture suspected to contain cerebrospinal fluid, be diluted before application to the sample pad portion of the later flow device. An exemplary dilution of the sample is 100×, using, e.g., phosphate-buffered saline at pH 7.4; a surfactant (e.g., Surfactant 10G). and polyvinylpyrrolidone (average molecular weight 29k),

TABLE 1

Example of dilution procedure to obtain 200 uL of diluted sample

| Components | Stock conc. | Final conc. | Volume |
|---|---|---|---|
| PVP (29K) | 20% in 1X PBS (W/V) | 1% | 10 ul |
| S10G | 20% in 1X PBS (W/V) | 0.5% | 5 ul |
| Clinical samples | 100% | 1% | 2 ul |
| 1X PBS (pH 7.4) | 1X | — | 183 ul |

Experimental results showed that simply depending on binding of an asialo-transferrin to anti-transferrin antibodies was insufficiently accurate to give reliable results in actual clinical examples and gave rise to false negatives. This could lead to serious consequences for the patient who has undergone neurosurgery. In contrast, the addition of the serum line with the cut-off values empirically determined, when used in addition to the anti-transferrin antibody line, gave 100% accurate determination in the samples tested.

The methods of devices herein employ a competitive reaction at the serum line, and an anti-antigen binding reaction at the antibody line. For example, in the case of the asialo-transferrin detection technology, with a pure serum sample (i.e., not diluted with CSF) the glycoprotein-binding AuNP conjugate (see, e.g., conjugate I in FIG. 1) will bind the many available serum glyco sites while in the conjugate pad portion, thus leaving very few or none available for binding when the sample flows over the serum line of the binding portion. This results in an undetectable, or very weak signal (below the cut-off value) at the serum line. In addition, there will only be a very a small quantity of the TF-binding AuNP conjugate (see, e.g., conjugate II in FIG. 1) because of causing a Hook Effect, thus leading to a very weak antibody line signal in the binding portion. This is illustrated in the first result column in FIG. 2, where the pure serum sample shows no serum line and a very weak antibody line. In contrast, in a sample containing serum diluted by the presence of CSF, the glycoprotein binding AuNP conjugate (see, e.g., conjugate I in FIG. 1) will bind the fewer glyco sites of the sample in the conjugate pad portion, thus leaving some conjugate I available for binding when the sample flows over the serum line of the binding portion. This results in a detectable signal (at or above the cut-off value) at the serum line. In addition, there will be a quantity of the TF-binding AuNP conjugate (see, e.g., conjugate II in FIG. 1), not causing a Hook Effect, thus leading to antibody line signal in the binding portion. However, given the already-small amount of asialo-transferrin in any sample, the line may not be strong. Accordingly, it is important to tune the cut-off value. This is illustrated in the second result column in FIG. 2, where the sample shows a serum line and an antibody line. The clinical samples (negative, positive, positive, and negative) shown in FIG. 2 demonstrate the test strip working on actual clinical examples distinguishing between CSF-containing ("P") and CSF-free ("N") samples.

FIG. 3 shows an empirical determination of the required cut off values using clinical samples known to be positive or negative by other methods, as well as control buffer, pure serum and pure CSF. The samples are diluted (e.g., ×100) in order to overcome Hook effect problems and to reduce non-specific signals. Optical intensity was measured with a NanoBioLife NGR-100 optical reader (NanoBioLife, Eobusaet-gil, Geumcheon-gu, Seoul, Republic of Korea). In the example shown, the following the cut-off values were determined: Serum line>250/TF Ab>60. The cut-off value were determined by their distinguishing the positive and negative samples. This leads to the following conclusions: serum line–positive/TF Ab line–negative=results of control only (buffer); serum line—negative/TF Ab line–positive=results of negative samples normally; serum line—positive/TF Ab line–positive=results of positive sample. Thus, in a manner, the antibody line can be thought of as an on/off visual indicator of asialo-transferrin, whereas the serum line confirms whether there is CSF diluting the sample. The control line is preferably added for the working test strip to confirm that the sample has actually flowed down the test strip, so as to avoid false negatives from defective strips/defective sample flow (such as a leak).

The device using the serum line technology can be made to detect beta-trace protein instead of asialo-transferrin. Beta-trace protein, a 168 amino acid glycoprotein which has a low molecular weight of 23,000 to 29,000 Da, depending on the degree of glycosylation, is largely confined to the CSF. However, it is not only present in the CSF and can, for example, also be present when impaired renal function occurs. In addition, it does naturally already occur in low concentrations in the blood. Thus, a testing technology that relies on just detecting the presence of beta-trace protein in the blood is susceptible to problems and false results. To overcome these problems, the present disclosure uses an additional serum line technology, as used with the asialo-transferrin detection technology. Combining the serum line technology and beta-trace protein detection (via anti-beta-trace protein antibodies) can provide unprecedented accuracy in detection of CSF leaks in patient samples.

Rapid and sensitive detection of CSF is crucial [24] to make real-time critical decisions regarding patient care. For example, if a CSF leakage occurs post-surgery, a patient may need to quickly return to the operating room to explore and repair the CSF leak, which would in turn treat the positional headaches and potential infection from contact with contaminated areas and the increased risk of developing meningitis. At the time fluid is first noticed, and if the surgeon is unsure whether the fluid contains CSF, the surgeon can often only wait hours or days for confirmatory analysis, which delays action and can lead to poorer patient prognosis. In some cases, a patient might not even have a classic presentation of a positional headache, which can further delay the diagnosis of a CSF fluid leak. Thus, a rapid test that can be used in the surgery to detect the presence of CSF fluid would allow neurosurgeons to make immediate clinical decisions leading to improved patient outcomes.

Conceptually, the lateral flow immunoassay constructed herein can be considered in the following way:
  to distinguish human bodily fluid (i.e., serum and CSF)
    from water or buffer (false positive)
  serum line intensity (T2): serum<CSF<buffer
  antibody line intensity (T1): buffer<serum<CSF
    →This is why the calculation is <$T1^2 \times T2$>

Chemicals and Reagents

Bovine serum albumin (30-AB74), and surfactant 10G (95R-103) were purchased from Fitzgerald Industries International (Acton, MA, USA), and human anti-transferrin monoclonal antibody (4T15-11D3; immobilized, 4T15-8B9; conjugated) was purchased from HyTest Ltd. (Turku, Finland). Biotinylated *Sambucus nigra* lectin (B-1305) were from Vector laboratories (Burlingame, CA, USA), and Amicon® Ultra 0.5 mL 30K/100K Centrifugal Filters (UFC501096/UFC510096) were purchased from Merck Millipore (Billerica, MA, USA), and Absorbent (Grade 222), conjugate (8964), and sample pads (Grade 222) were purchased from Alshtrom-Munksjo (Helsinki, Finland). Gold nanoparticles (EM.GC40) was purchased from BB international (Cardiff, UK), and Zeba™ Spin Desalting Columns, 7K MWCO (89891), spin column tubes (697245), and borate buffer (28341) were purchased from Thermo Scientific (Rockford, MD, USA), respectively. Phosphate buffered saline (PR2007) and sodium acetate buffer (S2022) were purchased from Biosesang Co. (Sungnam, Korea). Neo protein saver (NPS-301) was purchased from TOYOBO Co., LTD. (Osaka, Japan). An anti-mouse IgG antibody produced in goat (M8642), human serum (H4522), streptavidin (S4762), boric acid (B6768), sodium tetraborate decahydrate (S9640), polyvinylpyrrolidone (29K) (234257), skim milk powder (70166), D-(+)-Trehalose dehydrate (T5251), sodium (meta)periodate (51878), Triton™ X-100 (X100), TWEEN® 10 (P1379) and all other chemicals were purchased from Sigma-Aldrich Co. (St. Louis, MO, USA). All reagent solutions were dissolved in distilled water passed through an ELGA purification system (Lane End, UK).

Preparation of Oxidized Antibody

All Anti-transferrin antibodies were oxidized to remove sialic acid residues binding to the sialic acid-specific lectin from the glycan chains. 1 mM sodium metaperiodate in 0.1M sodium acetate buffer (pH 5.2) was added to antibody solution, and incubated it at 4° C. half-hour, and the sodium metaperiodate was removed by passing through desalting resin-filled eppendorf tube with 450 μL of phosphate-buffered saline (PBS) at 1,000×g, 5 min. After repeating washing step for 3 times, the antibody solution was treated with 10 mg mL−1 bovine serum albumin (BSA) in 1×PBS (10:90, v/v), and was incubated at room temperature, 1.5 hour. After the incubation, unbounded BSA was removed by passing through centrifugal ultrafiltration with 450 μL of PBS at 12,000×g, 20 min. After filtration, antibody-BSA complex was dissolved in 1×PBS with the concentration of 1 mg mL$^{-1}$ based on the initial amount of antibody, and was stored until use.

Preparation of Gold Nanoparticles Conjugates

Two types of conjugates are used in this research; 1) gold nanoparticles-streptavidin-biotinylated lectin conjugate (AuNP-STA-biotin lectin); 2) gold nanoparticles-transferrin antibody conjugate (AuNP-TF antibody). For AuNP-STA-biotin lectin conjugate, streptavidin (10 μL, 1 mg mL−1) was added to a mixture of AuNP colloid (40 nm in diameter, 1x AuNP, $\lambda_{max}$ O.D.=1.0, 1 mL) and borate buffer (100 μL, 0.1M, pH 8.5), and the mixture was incubated for 30 min at room temperature. After the incubation, bovine serum albumin dissolved in 1× phosphate buffered saline (10 μL, 100 mg mL$^{-1}$) was added for blocking the AuNP surface, and the mixture was incubated for an hour at room temperature. After the incubation, the mixture was centrifuged using a refrigerated micro centrifuge at 6,448×g, 10° C. for 15 min. The supernatant was discarded, and the AuNP conjugate was suspended with borate buffer (1 mL, 10 mM, pH 8.5). The centrifugation and suspension steps were repeated third. AuNP-STA conjugate was re-suspended with PBS (1 mL, 1X) for next incubation. Biotinylated lectin (10 μL, 1 mg mL$^{-1}$) was added to AuNP-STA conjugate solution, and the mixture was incubated for 15 min at room temperature. After the incubation, biotin (5 μL, 5 mg mL$^{-1}$) was added for blocking, and the mixture was incubated for another 15 min at room temperature. After the incubation, the mixture was centrifuged to remove unreacted materials as described above. AuNP-STA-biotin lectin conjugate was finally re-suspended and concentrated 10-fold with storage buffer (5% trehalose, 0.5% protein saver, 0.2% tween-20, 1% triton X100 in 1×PBS), and stored at 4° C. For AuNP-TF antibody conjugate, transferrin antibody (10 μL, 1 mg mL$^{-1}$) was added to a mixture of AuNP colloid (40 nm in diameter, 1×AuNP, O.D.=1.0, 1 mL) and borate buffer (100 μL, 0.1M, pH 8.5), and the mixture was incubated for 30 min at room temperature. After the incubation, neo protein saver dissolved in 1×PBS (50 μL, 100 mg mL$^{-1}$) was added for blocking the AuNP surface, and the mixture was incubated for an hour at room temperature. After the incubation, the mixture was centrifuged to removed unreacted materials as described above, and the conjugate was finally re-suspended and concentrated 10-fold with storage buffer.

Preparation of a Lateral Flow Immunoassay Strip Sensor

To carry out a LFI strip sensor, 0.25 mg mL$^{-1}$ of antibody which binds mouse IgG, 1:100 diluted human serum, and 0.5 mg mL−1 of anti-transferrin antibody were immobilized on a membrane (1 μL cm$^{-1}$) for control line, serum line, and test line, respectively; all distance between each line were approximately 3 mm. Two types of AuNP conjugate solution (170 μL, 4-fold concentration for AuNP-STA-biotin lectin; 3-fold concentration for AuNP-TF antibody) with storage buffer were applied to the conjugate pad (80×4 mm$^2$). After dry the loaded membrane and conjugate pad 37° C. for 15 min, an absorbent pad was attached to the top of the membrane with a 2 mm overlap. Two conjugate pads also were attached to the bottom of the membrane, and a sample pad was placed underneath it to load the sample. The assembled strip was stored in a humidity-controlled chamber (21° C. and 23% relative humidity) before use.

Results II

A Hook effect-based LFI sensor disclosed herein successfully discriminated positive clinical CSF samples from negative samples with statistical significance (positive vs. negative t-test; p=0.000013), 92.31% sensitivity, and 100% specificity. The LFI sensor described in this study offers fast, highly specific, highly sensitive and easy to use POC test for CSF leak detection in situations such as neurological surgery and in the ER.

Cerebrospinal fluid (CSF) is a colorless liquid from the brain and spinal cord (1) that serves multiple functions including nutritional, waste removal, and cushioning (2-4). A CSF leak can occur through the nose or ear canal iatrogenically or traumatically (5-8), and can occur spontaneously, intraoperatively or postoperatively after spinal and cranial surgery (9-12). A CSF leak that occurs postoperatively, particularly after lumbar and skull surgery, can result in low pressure headaches (13, 14), meningitis (15, 16), and central nervous system infections (17, 18). Therefore, a rapid and accurate method to detect the presence of post-operative CSF leak is essential for timely treatment of such conditions.

Symptoms of CSF leak are often confused with migraine or other cerebrospinal disorders (19), and it is not easy to diagnose. Migraine and CSF leak can have overlapping symptoms such as headaches, nausea, and sensitivity to light or sound, causing diagnostic errors (20). Currently the gold-standard for the detection of CSF in a fluid sample is gel electrophoresis which is costly, time-consuming, and requires expensive equipment and expert training (21-23). Recently, in the pursuit of a rapid and simple CSF leak diagnostic, several groups have started to study an asialo-transferrin (beta2-transferrin, β2TF), which is specifically found in CSF (24-26). β2TF is a modified glycoprotein from a sialo-transferrin (sTF) through brain neuraminidase in the CSF (27, 28). This enzyme eliminates terminal sialic acid residues on the glycan chains of sialylated transferrin (TF) (29, 30), resulting in β2TF constituting up to 30% of total TF in CSF (31, 32). However, anti-transferrin (TF) antibodies can barely distinguish β2TF from sTF because the amount present is relatively low and the chemical structure derived from the enzyme has high similarity. There are only a few studies of CSF leak diagnosis using anti-β2TF antibodies (24-26); however, they suffer from limitations in terms of assay time, sensitivity, and specificity which are insufficient for point-of-care (POC) diagnosis.

Herein, we have developed a simple detection method that can allow CSF leak diagnosis using two types of conjugates with two detection zones utilizing the well-known hook effect phenomenon. We synthesized two different gold nanoparticle conjugates: i) an anti-TF antibody-immobilized gold nanoparticles conjugate (AuNPs/Ab) providing an antibody line in the detection zone, which acts as a sandwich immunoassay between two antibodies with TF, and ii) a lectin-immobilized gold nanoparticle conjugate (AuNPs/lectin) providing a serum line in the detection zone for binding between lectin and sialo-glycoprotein (S GP).

The hook effect is a well-known immunologic phenomenon, resulting in a negative signal from an immunoassay when samples contain an analyte concentration that is too high (33, 34). Under conventional circumstances, this phenomenon can cause false-negative results, and many immunological studies deliberately try to avoid this situation in order to improve accuracy. In this study, however, the hook effect has been harnessed to improve accuracy and plays a key role. We hypothesized that the hook effect can be availed to improve accuracy for the purpose of CSF leak detection. Since TF and SGP exist in high concentrations in the serum, AuNPs/Ab and AuNPs/lectin conjugates will fully react with TF and SGP, respectively. Consequently, there will be no remaining binding sites left for the anti-TF antibodies of the downstream antibody line and the SGP of the serum line, and the fully TF- and SGP-bound conjugates will therefore flow past the detection zones, leaving no signal line. In contrast, because the CSF has overall less TF and SGP per unit volume of the sample as compared to the serum (thus avoiding the hook effect), the TF- and SGP-bound conjugates in a CSF-diluted serum sample will have some binding sites open and able to bind to the fixed anti-TF antibodies of the antibody line and the SGP of the serum line. This novel methodology should show no signal when the sample contains serum and a double line positive result when the sample contains CSF, i.e., negative and positive results for CSF leak, respectively. Two types of conjugates were used to improve the test accuracy, and a formular was developed, as a function of both signal responses, to improve the classification of true negative and positive samples. The methodology, development, optimization and testing of this new method for CSF leak detection are described below.

Materials and Methods

Materials

Human anti-TF monoclonal antibody (4T15-11D3; immobilized, 4T15-8B9; conjugated) was purchased from HyTest Ltd. (Turku, Finland), and biotinylated *Sambucus nigra* lectin (B-1305) was purchased from Vector Laboratories (Burlingame, CA, USA). Gold nanoparticles (EM.GC40) were purchased from BB international (Cardiff, UK). Borate buffer (28341), Zeba spin desalting columns, 7K MWCO (89891), and spin column tubes (697245) were purchased from Thermo Scientific (Waltham, MA, USA). Amicon Ultra 0.5 mL 30K/100K centrifugal filters (UFC501096 and UFC510096) were purchased from Merck Millipore (Billerica, MA, USA), and absorbent (Grade 222), conjugate (8964), and sample pads (Grade 222) were purchased from Alshtrom-Munksjo (Helsinki, Finland). Bovine serum albumin (BSA, 30-AB74), and surfactant 10G (S10G, 95R-103) were purchased from Fitzgerald Industries International (Acton, MA, USA). Phosphate buffered saline (PBS, PR2007) and sodium acetate buffer (S2022) were purchased from Biosesang Co. (Sungnam, Korea). Neo protein saver (NPS-301) was purchased from TOYOBO (Osaka, Japan). Pooled human cerebrospinal fluid (IRHUCSF1ML) was purchased from innovative research (Novi, MI, USA). An anti-mouse IgG antibody produced in goat (M8642), human serum (H4522), streptavidin (S4762), boric acid (B6768), sodium tetraborate decahydrate (S9640), polyvinylpyrrolidone (29K) (PVP, 234257), skim milk powder (70166), D-(+)-trehalose dehydrate (T5251), sodium (meta)periodate (S1878), Triton X-100 (X100), TWEEN 10 (P1379) and all other chemicals were purchased from Sigma-Aldrich (St. Louis, MO, USA). All reagent solutions were dissolved in distilled water passed through an ELGA purification system (Lane End, UK).

Preparation of Oxidized Antibody

All anti-TF antibodies were oxidized to remove sialic acid residues from the glycan chains which can bind to the sialic acid-specific lectin. 1 mM sodium metaperiodate in 0.1 M sodium acetate buffer (pH 5.2) was added to the antibody solution, incubated at 4° C. for 30 min, and the sodium metaperiodate was removed by passing the solution through a desalting resin-filled Eppendorf tube with 450 μL of PBS at 1,000×g for 5 min. After washing 3 times, the antibody solution was treated with 10 mg/mL BSA in 1×PBS (10:90, v/v) and was incubated at 25° C. for 90 min. After incubation, unbound BSA was removed by passing through 100K centrifugal ultrafiltration with 450 μL PBS at 12,000×g for 20 min. After filtration, antibody-BSA complexes were dissolved in 1×PBS at 1 mg/mL based on the initial amount of antibody and was stored until use.

Preparation of Gold Nanoparticle Conjugates

Two types of conjugates were used in this study: i) a gold nanoparticle-streptavidin-biotinylated lectin conjugate (AuNPs/lectin) and ii) a gold nanoparticle-TF antibody conjugate (AuNPs/Ab). For the AuNPs/lectin conjugate, streptavidin (10 μL, 1 mg/mL) was added to a mixture of AuNP colloid (40 nm in diameter, 1×AuNP, μmax O.D.=1.0, 1 mL) and borate buffer (100 μL, 0.1M, pH 8.5), and the mixture was incubated for 30 min at 25° C. After incubation, BSA dissolved in 1×PBS (10 μL, 100 mg/mL) was added to block the AuNP, and the mixture was incubated for 60 min at 25° C. After incubation, the mixture was centrifuged using a refrigerated micro centrifuge at 6,448×g at 10° C. for 15 min. The supernatant was discarded, and the AuNP conjugate was resuspended in borate buffer (1 mL, 10 mM, pH 8.5). The centrifugation and suspension steps were repeated 3 times. The AuNP-streptavidin conjugate was resuspended in 1 mL 1×PBS, biotinylated lectin (10 μL, 1 mg/mL) was added, and the mixture was incubated for 15 min at 25° C. After incubation, biotin (5 μL, 5 mg/mL) was added for blocking, and the mixture was incubated for another 15 min at 25° C. After incubation, the mixture was centrifuged to remove unreacted materials as described above. The AuNPs/lectin conjugate was finally resuspended and concentrated 10-fold with storage buffer (5% trehalose, 0.5% Neo protein saver, 0.2% Tween-20, 1% Triton X100 in 1×PBS), and stored at 4° C. For the AuNPs/Ab conjugate, TF antibody (10 µL, 1 mg/mL) was added to a mixture of AuNP colloid (40 nm in diameter, 1×AuNP, λmax O.D.=1.0, 1 mL) and borate buffer (100 µL, 0.1M, pH 8.5), and the mixture was incubated for 30 min at 25° C. After incubation, Neo protein saver dissolved in 1×PBS (50 µL, 100 mg/mL) was added to block the AuNP, and the mixture was incubated for 60 min at 25° C. After incubation, the mixture was centrifuged to removed unreacted materials as described above, and the conjugate was finally re-suspended and concentrated 10-fold with storage buffer.

Preparation of a Lateral Flow Immunoassay Sensor

To prepare a lateral flow immunoassay (LFI) sensor, 0.25 mg/mL of anti-mouse IgG antibody, 100-fold diluted human serum, and 0.5 mg/mL of anti-TF antibody were immobilized on a membrane (1 µL cm') for control, serum, and test lines, respectively, spaced 3 mm apart. Two types of AuNP conjugate solution (170 µL, 4-fold concentration for AuNPs/lectin; 3-fold concentration for AuNPs/Ab) with storage buffer were applied to the conjugate pad (80×4 mm$^2$). After drying the loaded membrane and conjugate pad at 37° C. for 15 min, an absorbent pad was attached to the top of the membrane with a 2-mm overlap. Two conjugate pads were also attached to the bottom of the membrane, and a sample pad was placed underneath it to load the sample. The assembled strip was stored in a humidity-controlled chamber (21° C. and 23% relative humidity) before use.

Optimization of Serum Concentration and the Dilution Factor

Different amounts of serum were immobilized on the membrane to evaluate the optimal concentration of serum as capture molecules for AuNPs/lectin conjugate. Human serum samples diluted 10-fold, 100-fold, and 1,000-fold were prepared in 1×PBS and immobilized on the membrane as a serum line. Different amounts (100-fold, 1,000-fold, and 10,000-fold diluted) of serum and CSF were diluted in sample buffer containing PVP (10 mg/mL) and S10G (5 mg/mL) dissolved in 1×PBS, and the solution was applied to the strip with 1×AuNPs/lectin conjugate. The image was captured with a ChemiDoc MP imaging system (Bio-Rad, Hercules, CA, USA).

Optimization of Antibody Line with Oxidation

Antibodies with or without oxidation were immobilized on the membrane for the immunoassay with the AuNPs/Ab conjugate. Different amounts (100-fold, 1,000-fold, and 10,000-fold diluted) of serum and CSF were diluted in the sample buffer containing PVP (10 mg/mL) and S10G (5 mg/mL) dissolved in 1×PBS, and the solution was applied to the strip with 1×AuNPs/Ab conjugate and AuNPs/lectin conjugate. The image was captured with a ChemiDoc MP imaging system.

Application of Samples to LFI Sensor

The sample buffer described in the previous section was prepared in an Eppendorf tube (198 µL), and 2 µL of serum, CSF, and clinical samples were taken and diluted in this sample buffer to a 1% final concentration. Only 100 µL of the diluted samples was applied to the LFI sensors, and the signal was measured after 10 min. The image was captured with a ChemiDoc MP imaging system, and the signal intensity was measured and analyzed using a portable detector (NBT-100; NanoBioTechnology, Anyang, South Korea).

Evaluation of Clinical Samples

In total 37 clinical samples were obtained from a Neurological Surgery, P.C. Rockville Centre, NY, USA (13 positive and 24 negative samples), and the institutional review board was approved by Gwangju Institute of Science and Technology (Approval number:20210217-BR-59-03-02). The clinical samples were stored at −80° C. for subsequent analysis, and 100 µL of 100-fold diluted clinical samples were applied to the LFI sensor. Acting as a standard reference method to evaluate clinical samples, β2TF was predetermined by a diagnostic service company (Quest Diagnostics, Secaucus, NJ, USA) (35). The image was captured with a ChemiDoc MP imaging system, and the signal intensity was measured and analyzed using a portable detector (NBT-100).

Evaluation of the portable detector

The color signal intensity from the NBT-100 portable detector (NanoBioTechnology, Anyang, South Korea) was compared with the ChemiDoc MP imaging system (Bio-Rad Laboratory, Hercules, CA, USA) to evaluate the portable detector's accuracy and reliability. The image was captured with the ChemiDoc MP, and the intensity of the strip was measured by the portable detector (NBT-100) and computational software (ImageLab 6.1, Bio-Rad). The measured intensities were then compared.

Statistical Analysis

All the statistical results including clinical sensitivity and specificity were calculated according to the Clinical and Laboratory Standards Institute EP12-A2 guideline.

Results and Discussion

Principle of LFI sensor: The LFI sensor for CSF leak detection is shown schematically in FIG. 8. The sensor consists of a sample pad, two conjugate pads, two detection lines and one control line on the membrane, and an absorbent pad. Two detection lines and two different conjugates are used in this device to improve the accuracy. In the detection lines, anti-TF antibody is immobilized as an antibody line, and human serum solution is immobilized as a serum line. For the conjugates, one conjugate is labeled with anti-TF antibody (AuNPs/Ab) which can react with transferrin, permitting a sandwich immunoreaction with another anti-TF antibody on the antibody line. Another conjugate is labeled with lectin (AuNPs/lectin) which can react with glycoprotein not only from the sample but also on the fixed serum line on the membrane, and a competitive reaction can ensue between them (FIG. 8(*b*)). When the sample is applied to the LFI sensor, the signal from the detection lines differs depending on the sample type (FIG. 8(*c*)).

With buffer, only the serum line can show a positive signal because there is no TF or glycoprotein present, causing the AuNPs/lectin conjugate to bind to the immobilized glycoprotein on the serum line, while the first conjugates flow past.

With CSF, both the antibody and serum lines show a positive signal. The positive antibody line signal results from the AuNPs/Ab conjugate capturing the TF from the sample and causing a sandwich immunoreaction with the immobilized anti-TF antibody on the antibody line. The positive serum line signal results from the glycoprotein from the sample and the serum line both competing for binding to the AuNPs/lectin conjugate. In this case, the concentration of glycoprotein from the serum line is higher in than the sample, which causes the AuNPs/lectin conjugate to bind mainly to the glycoprotein at the serum line.

In serum, both the antibody and serum lines show negative signals because there are "excessive" amounts of TF and glycoprotein. In this case, both AuNPs/Ab and AuNPs/lectin conjugates are fully bound by their "analytes", resulting in a lack of binding sites for the antibody or serum lines due to the hook effect. In summary, a TF concentration in CSF that is below the detection range concentration results in a positive signal, whereas a TF concentration in serum that is above the cutoff results in a negative signal.

To aid the leak detection classification, an empirical equation was developed as a function of the intensity of the antibody and serum lines, to improve accuracy. Furthermore, a portable detector was utilized providing rapid point-of-care (POC) diagnostic capability (FIG. 8 (d)).

Optimization of the LFI Sensor

The underpinning feature of the LFI sensor is whether the hook effect is shown or not in the two detection lines depending on the TF concentration of the samples. This was indeed confirmed. The hook effect is evident since no signal can be observed on the detection lines when the TF concentration of the sample is the same as that of the serum. In contrast, clear signals are detected from the detection line when the TF concentration of the sample is the same as that of the CSF (i.e., when the hook effect is avoided). In order to achieve the LFI platform to have a suitable cutoff concentration, extensive experimentation had to be conducted under various conditions.

Figures 9A, 9B, 9C, 9D:
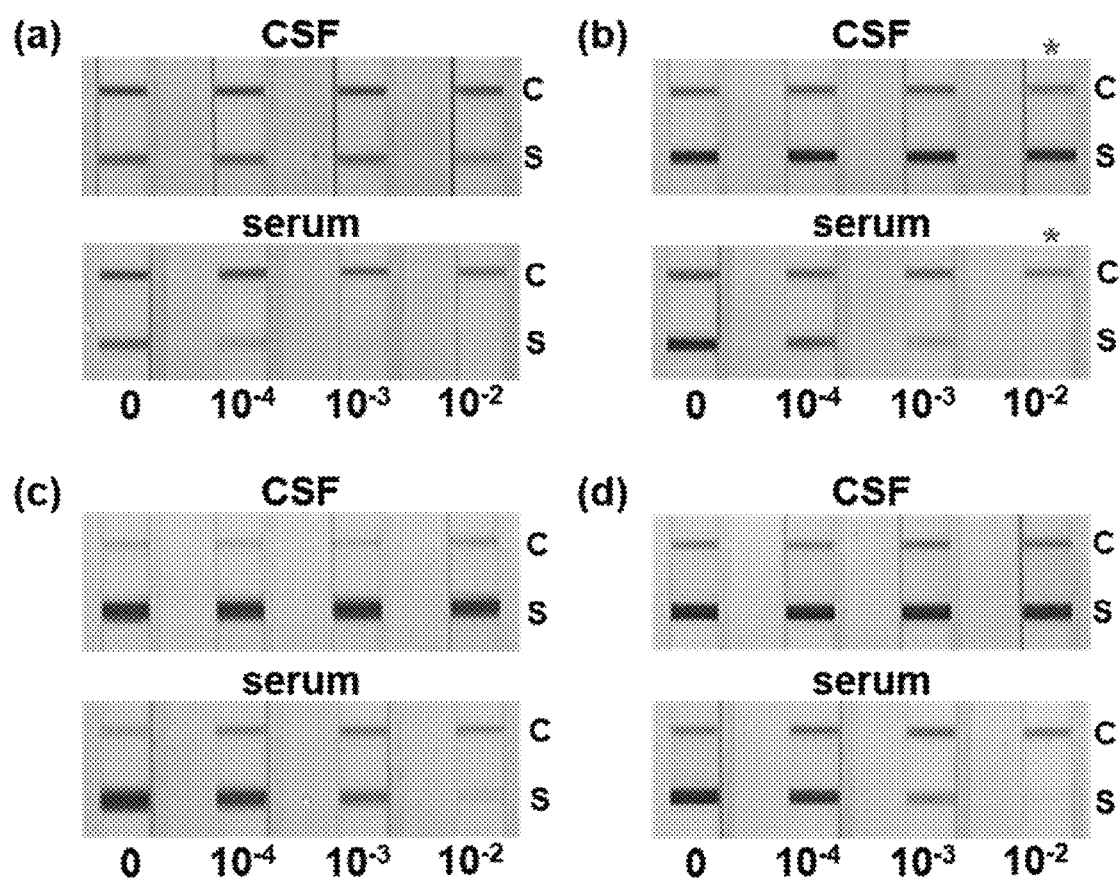
Figures 10A, 10B, 10C, 10D:
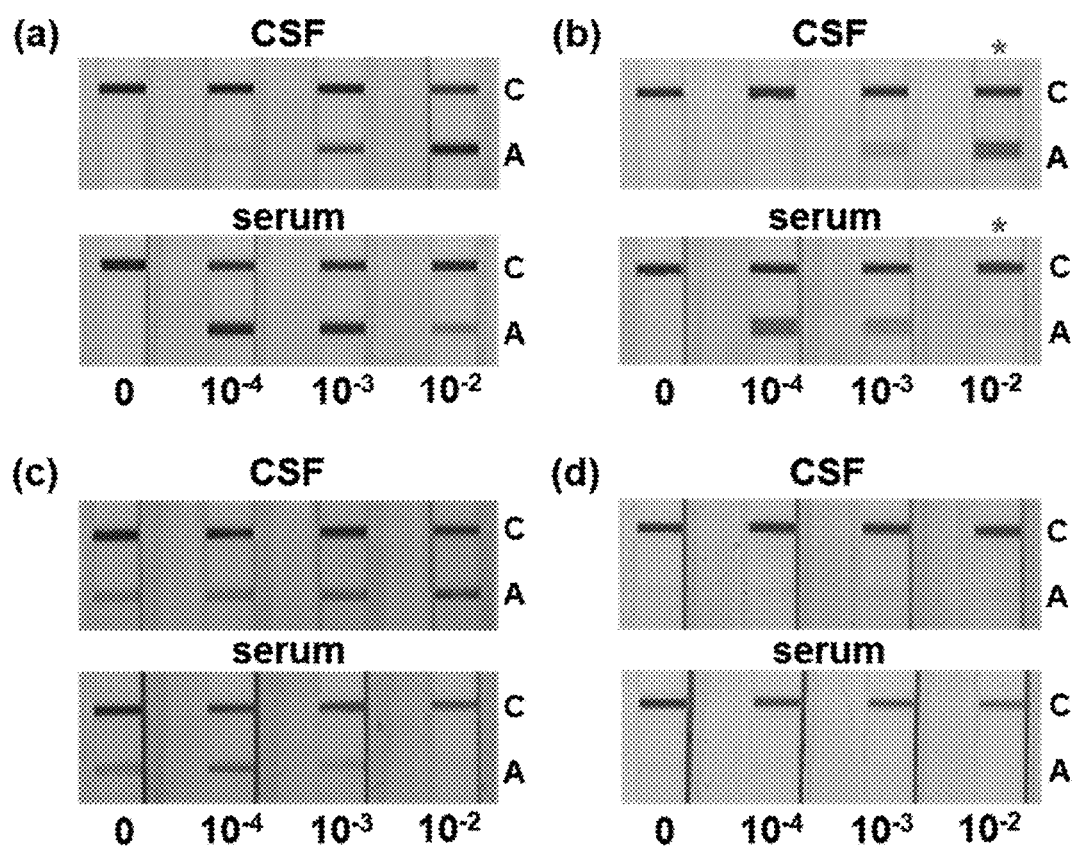

Firstly, the amount of glycoprotein immobilized on the serum line was optimized. We prepared diluted human serum: the serum was diluted in buffer 1-fold, 10-fold, 100-fold, or 1,000-fold. Then, the signal in each serum line was confirmed according to the sample concentration (FIG. 9). As a result, the strongest signal from CSF and a negative signal from serum were confirmed when 100-fold diluted glycoprotein was immobilized onto the serum line and when 100-fold diluted samples were used (FIG. 9(B)). The 1000-fold diluted glycoprotein in the serum line showed a weak signal from CSF (FIG. 9(A)), and the 10-fold diluted and undiluted glycoprotein in the serum line also showed signals from serum (FIGS. 9(C), 9(D)). Since the antibody has a glycan chain, we hypothesized that it may cause non-specific reactivity to other proteins and AuNPs/lectin conjugates. This phenomenon can be reduced by antibody oxidation. To confirm this, the antibody line signal with the two different AuNP conjugates was studied with and without antibody oxidation. The amount of antibody immobilized on the antibody line was the same as that in the general sandwich LFI, and the signal in each antibody line was confirmed according to the sample concentration (FIG. 10). The results showed a strong signal from CSF and a negative signal from serum with oxidized antibodies immobilized to the antibody line and for 100-fold diluted samples (FIG. 10(B)). In addition, non-oxidized antibodies showed greater non-specific reactivity in the serum sample (FIG. 10(C)).

Next, we confirmed the non-specific activity of antibodies depending on oxidation, and the results showed that the non-specific reactivity of antibodies to the AuNPs/lectin conjugate was significantly reduced when the oxidized antibody was immobilized on the detection line (FIGS. 10(C), 10(D)). In summary, we optimized three conditions for the developed LFI sensor: (i) when the serum line is immobilized using 100-fold diluted glycoprotein, (ii) when the antibody line is immobilized using oxidized antibodies, and (iii) when the sample dilution factor is 100-fold.

Evaluation of the Hook Effect in the Developed LFI Sensor

Next, we evaluated whether the hook effect occurs (or not) as expected in two detection lines in relation to the different sample types. CSF and serum samples prepared over a wider concentration range were loaded onto the LFI sensor (FIG. 11(A)), and the signals of each detection line were quantified. The hook effect in the CSF sample occurred over a concentration range of $10^{-2}$ to $10^{-1}$-fold dilution at the serum and antibody lines, respectively (FIG. 11(B)). In contrast, the hook effect in the serum sample occurred over a concentration range of $10^{-4}$ to $10^{-3}$-fold dilution at the serum and antibody lines, respectively (FIG. 11(C)). As a result, we confirmed that all conditions are well-optimized providing reliable utilization of the hook effect (or not, as the case may be) for both sample types.

Evaluation of the Developed LFI Sensor

We evaluated the final format of the developed LFI sensor with buffer, CSF, and serum samples. We applied 100-fold diluted sample to the optimized LFI sensor. As expected, only the serum line was detected with buffer, and both serum and antibody lines were detected with CSF. In contrast, neither detection line was detected from serum (FIG. 12(A)). To differentiate positive CSF signals from the buffer signal, the intensity was calculated using Eq. (1):

$$\text{Intensity (a.u.)} = I_{Ab}^2 \times I_{Serum} \tag{1}$$

where $I_{Ab}$ and ISerum are the intensities of the antibody and serum lines, respectively. Only CSF samples showed sufficiently high signal after applying the equation even though buffer samples have a high signal intensity at the serum line (FIG. 4b).

Clinical Sample Analysis

The optimized LFI sensor was validated using 37 clinical samples (13 positive and 24 negative samples) (Table 1). All of the samples were tested using both immunofixation and the LFI sensor. The results reported herein follow the standard guidelines for the reporting of diagnostic accuracy studies (STARD) (36-38).

TABLE 1

Lists of clinical samples with the results by the conventional method (immunofixation) and the developed lateral flow immunoassay (LFI) sensor. Cal. Int., calculated intensity; post-op, post-operative.

| Sample | | | LFI | | |
|---|---|---|---|---|---|
| No. | Leaking Place | Immunofixation | Serum | Antibody | Cal. Int. |
| 1 | Post op lumbar drain | Negative | Negative | Negative | Negative |
| 2 | Lumbar drain | Positive | Positive | Positive | Positive |
| 3 | Lumbar drain | Positive | Positive | Positive | Positive |
| 4 | Post op lumbar drain | Negative | Negative | Positive | Negative |
| 5 | Lumbar drain | Positive | Positive | Positive | Positive |
| 6 | Brain | Positive | Negative | Positive | Negative |
| 7 | Post op lumbar drain | Negative | Negative | Positive | Negative |
| 8 | Post op drain | Negative | Negative | Negative | Negative |
| 9 | Post op drain | Negative | Negative | Negative | Negative |

TABLE 1-continued

Lists of clinical samples with the results by the conventional method
(immunofixation) and the developed lateral flow immunoassay (LFI)
sensor. Cal. Int., calculated intensity; post-op, post-operative.

| Sample No. | Leaking Place | Immunofixation | LFI Serum | LFI Antibody | LFI Cal. Int. |
|---|---|---|---|---|---|
| 10 | Post op drain | Negative | Negative | Negative | Negative |
| 11 | Post op drain | Negative | Negative | Positive | Negative |
| 12 | Post op drain | Negative | Negative | Negative | Negative |
| 13 | Ventriculostomy | Positive | Positive | Positive | Positive |
| 14 | Post op drain | Negative | Negative | Negative | Negative |
| 15 | Post op drain | Negative | Negative | Negative | Negative |
| 16 | Lumbar wound | Negative | Negative | Negative | Negative |
| 17 | Lumbar wound | Negative | Negative | Negative | Negative |
| 18 | Lumbar wound | Negative | Negative | Negative | Negative |
| 19 | Lumbar wound | Negative | Negative | Negative | Negative |
| 20 | Lumbar wound | Negative | Negative | Negative | Negative |
| 21 | Brain ventric | Positive | Positive | Positive | Positive |
| 22 | Lumbar wound | Negative | Negative | Negative | Negative |
| 23 | Lumbar drain | Positive | Positive | Positive | Positive |
| 24 | Lumbar wound | Negative | Negative | Negative | Negative |
| 25 | Lumbar wound | Negative | Negative | Negative | Negative |
| 26 | Lumbar wound | Negative | Negative | Negative | Negative |
| 27 | Brain ventric | Positive | Positive | Positive | Positive |
| 28 | Brain ventric | Positive | Positive | Positive | Positive |
| 29 | Brain ventric | Positive | Positive | Positive | Positive |
| 30 | Brain ventric | Positive | Positive | Positive | Positive |
| 31 | Lumbar CSF drain | Positive | Positive | Positive | Positive |
| 32 | Lumbar wound | Negative | Negative | Negative | Negative |
| 33 | Lumbar wound | Negative | Negative | Negative | Negative |
| 34 | Lumbar wound | Negative | Negative | Negative | Negative |
| 35 | Brain ventric | Positive | Positive | Positive | Positive |
| 36 | Lumbar wound | Negative | Negative | Positive | Negative |
| 37 | Lumbar wound | Negative | Negative | Negative | Negative |

The LFI sensor could clearly discriminate between positive and negative samples (FIGS. 13(A), 13(B); positive vs. negative t-test; p=1.36E-05), and a noticeable separation is readily identifiable when the detection line responses are plotted in two-dimensions FIG. 15). Since the aim of using two detection lines and two conjugates was to improve the degree of classification accuracy for CSF leak detection, we also plotted the receiver operating characteristic (ROC) curve using only the serum or antibody line (FIG. 13(C)). The area under the curve (AUC) is a measure of the accuracy of a diagnostic test, and a result of 0.9676, 0.9616, and 0.9910 is achieved for the serum line, antibody line, and the calculated intensity (a function of both the serum and antibody lines), respectively (Table 2).

TABLE 2

Specification of the developed lateral flow immunoassay
sensor for cerebrospinal fluid leak detection.

| | Serum line | Antibody line | Calculated Intensity |
|---|---|---|---|
| Area under the curve | 0.9676 | 0.9616 | 0.9910 |
| Sensitivity | 92.31% | 100% | 92.31% |
| Specificity | 96% | 84% | 100% |
| Youden's index (J) | 0.883 | 0.84 | 0.923 |

*The samples for this specification include 37 clinical samples (positive n = 13, negative n = 24) and one blank samples (buffer only).

This result confirmed that the accuracy of the LFI sensor has improved by using two detection lines and two conjugates. It is likely that the significance of the improvement would become even more apparent with a larger sample size. In addition, the specificity of the LFI sensor was found to be 100% when using the calculated intensity, even though the sensitivity was 92.31% which is lower than the antibody line in isolation (Table 2). However, by calculating Youden's index (J) (39) from the ROC curve, it was confirmed that the combined approach, using the calculated intensity, is the preferred method (yielding a score of J=0.923) rather than using only one detection line (J=0.883). The performance evaluation of the LFI sensor is summarized in Table 2.

CONCLUSION

A novel LFI sensor, which exploits the well-known hook effect, has been successfully developed for the detection of CSF leakage from clinical samples. The LFI sensor was designed and optimized with two detection lines and two different conjugates to improve accuracy, and initial clinical effectiveness of this approach was demonstrated by testing with 37 patient samples. The LFI sensor clearly distinguished between positive and negative samples (positive vs. negative t-test; p=1.36E-05), and ROC analysis confirmed that it can be used to detect CSF leakage. The sensitivity and the specificity of the LFI sensor was found to be 92.31% and 100%, respectively, with improved diagnostic performance compared to the use of a single detection line. Furthermore, the test is readily amenable for POC testing and the total sample-to-answer time is only ~10 min, which is the fastest detection method known up to this point. The specificity of our novel approach, which utilizes the hook effect, could be improved further by generating an antibody that is more specific to TF in CSF. Future work will test our approach with more samples that a robust classification model can be built. The clinical data presented herein naturally clusters and a simple supervised machine learning algorithm should enable accurate predictions with little risk of overfitting. In practice, such a model could be readily integrated on-chip as part of a POC device to provide an automated classification response to a healthcare practitioner, without any interpretation being required. We can conclude that the proof of concept LFI sensor developed herein shows exceptional potential for routine clinical use at the point-of-care, to enable early diagnosis of CSF leakage, which can especially benefit those patients recovering from spinal surgery.

REFERENCES

1. Conly J M, Ronald A R. Cerebrospinal fluid as a diagnostic body fluid. The American journal of medicine 1983; 75 1:102-8.
2. Di Terlizzi R, Platt S. The function, composition and analysis of cerebrospinal fluid in companion animals: part I—function and composition. Vet J 2006 November; 172 3:422-31. Epub 2005/09/13 as doi: 10.1016/j.tvjl.2005.07.021.
3. Pollay M. The function and structure of the cerebrospinal fluid outflow system. Cerebrospinal fluid research 2010; 7 1:1-20.
4. Engelhardt B, Sorokin L. The blood-brain and the blood-cerebrospinal fluid barriers: function and dysfunction. Semin Immunopathol 2009 November; 31 4:497-511. Epub 2009/09/26 as doi: 10.1007/s00281-009-0177-0.
5. Daele J, Goffart Y, Machiels S. Traumatic, iatrogenic, and spontaneous cerebrospinal fluid (CSF) leak: endoscopic repair. B-ent 2011; 12:47.
6. Kovalerchik O, Mady L J, Svider P F, Mauro A C, Baredes S, Liu J K, Eloy J A. Physician accountability in iatrogenic cerebrospinal fluid leak litigation. Int Forum Allergy Rhinol 2013 September; 3 9:722-5. Epub 2013/03/29 as doi: 10.1002/alr.21169.
7. Bedrosian J C, Anand V K, Schwartz T H. The endoscopic endonasal approach to repair of iatrogenic and noniatrogenic cerebrospinal fluid leaks and encephaloceles of the anterior cranial fossa. World Neurosurg 2014 December; 82 6 Suppl:S86-94. Epub 2014/12/17 as doi: 10.1016/j.wneu.2014.07.018.
8. Hicks G W, Wright Jr J W, Wright III J W. Cerebrospinal fluid otorrhea. The Laryngoscope 1980; 90 S25:1-25.
9. Wong J M, Ziewacz J E, Ho A L, Panchmatia J R, Bader A M, Garton H J, Laws E R, et al. Patterns in neurosurgical adverse events: cerebrospinal fluid shunt surgery. Neurosurg Focus 2012 November; 33 5:E13. Epub 2012/11/03 as doi: 10.3171/2012.7.FOCUS12179.
10. Selesnick S H, Liu J C, Jen A, Newman J. The incidence of cerebrospinal fluid leak after vestibular schwannoma surgery. Otology & Neurotology 2004; 25 3:387-93.
11. Schlosser R J, Bolger W E. Nasal cerebrospinal fluid leaks: critical review and surgical considerations. The Laryngoscope 2004; 114 2:255-65.
12. Stankiewicz J A. Cerebrospinal fluid fistula and endoscopic sinus surgery. The Laryngoscope 1991; 101 3:250-6.
13. Lay C M. Low cerebrospinal fluid pressure headache. Current Treatment Options in Neurology 2002; 4 5:357-63.
14. Marcelis J, Silberstein S D. Spontaneous low cerebrospinal fluid pressure headache. Headache: The Journal of Head and Face Pain 1990; 30 4:192-6.
15. Bernal-Sprekelsen M, Bleda-Vazquez C, Carrau R L. Ascending meningitis secondary to traumatic cerebrospinal fluid leaks. American journal of rhinology 2000; 14 4:257-60.
16. Ivan M E, Iorgulescu J B, El-Sayed I, McDermott M W, Parsa A T, Pletcher S D, Jahangiri A, et al. Risk factors for postoperative cerebrospinal fluid leak and meningitis after expanded endoscopic endonasal surgery. J Clin Neurosci 2015 January; 22 1:48-54. Epub 2014/12/03 as doi: 10.1016/j.jocn.2014.08.009.
17. Abuabara A. Cerebrospinal fluid rhinorrhoea: diagnosis and management. Medicina Oral, Patologia Oral y Cirugia Bucal (Internet) 2007; 12 5:397-400.
18. Kulkarni A V, Drake J M, Lamberti-Pasculli M. Cerebrospinal fluid shunt infection: a prospective study of risk factors. Journal of neurosurgery 2001; 94 2:195-201.
19. Schievink W I. Spontaneous spinal cerebrospinal fluid leaks and intracranial hypotension. Jama 2006; 295 19:2286-96.
20. Madsen S A, Fomsgaard J S, Jensen R. Epidural blood patch for refractory low CSF pressure headache: a pilot study. J Headache Pain 2011 August; 12 4:453-7. Epub 2011/04/05 as doi: 10.1007/s10194-011-0331-7.
21. Ryali R G, Peacock M K, Simpson D A. Usefulness of 02-transferrin assay in the detection of cerebrospinal fluid leaks following head injury. Journal of neurosurgery 1992; 77 5:737-9.
22. Papadea C, Schlosser R J. Rapid method for beta2-transferrin in cerebrospinal fluid leakage using an automated immunofixation electrophoresis system. Clin Chem 2005 February; 51 2:464-70. Epub 2004/12/21 as doi: 10.1373/clinchem.2004.042697.
23. Mantur M, Lukaszewicz-Zajac M, Mroczko B, Kulakowska A, Ganslandt O, Kemona H, Szmitkowski M, et al. Cerebrospinal fluid leakage—reliable diagnostic methods. Clin Chim Acta 2011 May 12; 412 11-12:837-40. Epub 2011/02/22 as doi: 10.1016/j.cca.2011.02.017.
24. Kita A E, Bradbury D W, Taylor Z D, Kamei D T, St John M A. Point-of-Care Cerebrospinal Fluid Detection. Otolaryngol Head Neck Surg 2018 November; 159 5:824-9. Epub 2018/07/25 as doi: 10.1177/0194599818789075.
25. Bradbury D W, Kita A E, Hirota K, St John M A, Kamei D T. Rapid Diagnostic Test Kit for Point-of-Care Cerebrospinal Fluid Leak Detection. SLAS Technol 2020 February; 25 1:67-74. Epub 2019/09/24 as doi: 10.1177/2472630319877377.
26. Chou C-H, Huang T-H, Hsieh P-C, Ho N Y-J, Chen C-A, Wu K, Tsai T-T. Quantitative lateral flow immunoassay for rapid detection and monitoring of cerebrospinal fluid leakage following incidental durotomy. Analytica Chimica Acta 2022:339544.
27. Nandapalan V, Watson I, Swift A. Beta-2-transferrin and cerebrospinal fluid rhinorrhoea. Clinical Otolaryngology & Allied Sciences 1996; 21 3:259-64.
28. Oh J, Kwon S J, Dordick J S, Sonstein W J, Linhardt R J, Kim M G. Determination of cerebrospinal fluid leakage by selective deletion of transferrin glycoform using an immunochromatographic assay. Theranostics 2019; 9 14:4182-91. Epub 2019/07/10 as doi: 10.7150/thno.34411.
29. Morgan E, Laurell C-B. Neuraminidase in mammalian brain. Nature 1963; 197 4870:921-2.
30. Kelly R T, Farmer S, Greiff D. Neuraminidase activities of clinical isolates of Diplococcus pneumoniae. Journal of bacteriology 1967; 94 1:272-3.
31. Hoffmann A, Nimtz M, Getzlaff R, Conradt H S. 'Brain-type' N-glycosylation of asialo-transferrin from human cerebrospinal fluid. FEBS letters 1995; 359 2-3: 164-8.
32. Brown K J, Vanderver A, Hoffman E P, Schiffmann R, Hathout Y.

Characterization of Transferrin Glycopeptide Structures in Human Cerebrospinal Fluid. Int J Mass Spectrom 2012 Feb. 15; 312:97-106. Epub 2012/03/13 as doi: 10.1016/j.ijms.2011.06.021.
33. Fernando S A, Wilson G S. Studies of the 'hook' effect in the one-step sandwich immunoassay. Journal of immunological methods 1992; 151 1-2:47-66.
34. Tate J, Ward G. Interferences in immunoassay. The clinical biochemist reviews 2004; 25 2:105.
35. Schnabel C, Di Martino E, Gilsbach J M, Riediger D, Gressner A M, Kunz D. Comparison of β2-transferrin and β-trace protein for detection of cerebrospinal fluid in nasal and ear fluids. Clinical Chemistry 2004; 50 3:661-3.
36. Bossuyt P M, Reitsma J B, Bruns D E, Gatsonis C A, Glasziou P P, Irwig L M, Moher D, et al. The STARD statement for reporting studies of diagnostic accuracy: explanation and elaboration. Annals of internal medicine 2003; 138 1:W1-12.
37. Bossuyt P M, Reitsma J B, Bruns D E, Gatsonis C A, Glasziou P P, Irwig L M, Lijmer J G, et al. Towards complete and accurate reporting of studies of diagnostic accuracy: the STARD initiative. Radiology 2003; 226 1:24-8.
38. Bossuyt P M, Reitsma J B, Bruns D E, Gatsonis C A, Glasziou P P, Irwig L, Lijmer J G, et al. STARD 2015: an updated list of essential items for reporting diagnostic accuracy studies. Clinical chemistry 2015; 61 12:1446-52.
39. Ruopp M D, Perkins N J, Whitcomb B W, Schisterman E F. Youden Index and optimal cut-point estimated from observations affected by a lower limit of detection. Biom J 2008 June; 50 3:419-30. Epub 2008/04/26 as doi: 10.1002/bimj.200710415.

What is claimed is:

1. A method of detecting the presence of cerebrospinal fluid in a liquid biological sample comprising:
   a) distributing the liquid biological sample on to a sample pad of a lateral flow device which comprises, in lateral flow sequence: a sample pad, a conjugate pad, a binding portion, and an absorbent pad, so as to permit the sample to flow along the lateral flow device; and wherein:
      (i) the conjugate pad thereof, downstream in lateral flow from the sample pad, comprises both (A) and (B) thereon, wherein:
         (A) is a first plurality of transferrin-binding antibodies conjugated to a first plurality of nanoparticles, and
         (B) is a plurality of lectin molecules conjugated to a second plurality of nanoparticles;
      (ii) the binding portion thereof, downstream in lateral flow from the conjugate pad, comprises the following separate domains:
         a. a domain which comprises a second plurality of transferrin-binding antibodies which are adhered to a surface of the lateral flow device;
         b. a dried blood serum domain reagent adhered to a surface of the lateral flow device;
   b) determining an intensity of an optical signal present at domain (ii)(a) and also at domain (ii)(b);
   c) calculating an optical value, wherein the optical value is determined as =(T1 intensity)$^2$×(T2 intensity), wherein T1 intensity is the optical signal intensity at domain (ii)(a), and T2 intensity is the optical signal intensity at domain (ii)(b), and determining if the optical value is above or below a pre-determined cut-off value for the lateral flow device, wherein if the optical value is above the predetermined cut-off value for the lateral flow device then the sample is identified as containing cerebrospinal fluid, and wherein if the optical value is below the pre-determined cut-off value for the lateral flow device then the sample is identified as not containing cerebrospinal fluid.

2. The method of claim 1, wherein, in the sample pad portion, the first plurality of transferrin-binding antibodies have been oxidized previously to remove sialic acid residues therefrom.

3. The method of claim 1, wherein, in the binding portion, the second plurality of transferrin-binding antibodies have been oxidized previously to remove sialic acid residues therefrom.

4. The method of claim 1, wherein the plurality of lectin molecules comprises *Sambucus nigra* lectin.

5. The method of claim 1, wherein the optical signals are determined using an optical reader device.

6. The method of claim 5, wherein the optical reader device further provides the optical value calculated in step c).

7. The method of claim 1, wherein the dried blood serum reagent domain adhered to the surface of the lateral flow device comprises human serum reagent.

8. The method of claim 1, wherein the liquid biological sample distributed on the sample pad portion has been diluted 90× to 110× with a buffer solution from a raw sample obtained from a human prior to sample being distributed on the sample pad portion and/or wherein a dried blood serum reagent has been diluted 90× to 100× prior to being adhered to the surface of the lateral flow device.

9. The method of claim 8, wherein the buffer solution comprises phosphate buffered saline comprising polyvinylpyrrolidone, a surfactant and is adjusted to pH 7.4.

10. The method of claim 1, wherein the sample comprise a blood, serum, otorrhea or rhinorrhea sample obtained from a human.

11. The methods of claim 1, wherein the predetermined cutoff value has been determined beforehand to account for Hook effect on binding of human serum glycoproteins to the dried blood serum reagent domain at concentrations of human serum glycoproteins in a non-diluted human serum sample and provide a positive signal.

12. The methods of claim 11, wherein the predetermined cutoff value has been determined beforehand such that human serum diluted 90× to 110× with a buffer solution from a previously-undiluted serum sample obtained from a human, wherein the sample is not diluted with cerebrospinal fluid and does not contain cerebrospinal fluid, gives an optical value below the predetermined cutoff value, or wherein the predetermined cutoff value has been determined beforehand such that human serum diluted 90× to 110× with a buffer solution from a previously-undiluted serum sample obtained from a human, wherein the sample is diluted with cerebrospinal fluid or does contain cerebrospinal fluid, gives an optical value below the predetermined cutoff value.

13. The method of claim 1, further comprising empirically determining the predetermined cutoff value beforehand by running a plurality of samples on the lateral flow device of human serum diluted 90× to 110× with a buffer solution from a previously-undiluted serum sample previously obtained from one or more humans, wherein the serum samples do not contain CSF, and calculating the optical value for each of the plurality of samples from (T1 intensity)$^2$×(T2 intensity), and selecting an optical value which is in excess of every one of the calculated optical values for each of the plurality of samples as the predetermined cutoff value.

14. The method of claim 1, further comprising empirically determining the predetermined cutoff value beforehand by (a) running a plurality of samples on the lateral flow device of human serum diluted 90× to 110× with a buffer solution from a previously-undiluted serum sample previously obtained from one or more humans, wherein the serum samples do not contain CSF, and calculating the optical value for each of the plurality of samples from (T1 intensity)$^2$×(T2 intensity), and (b) running a plurality of samples on the lateral flow device of human serum diluted 90× to 110× with a buffer solution from a previously-undiluted serum sample previously obtained from one or more humans, wherein the serum samples do contain CSF, and calculating the optical value for each of those plurality from (T1 intensity)$^2$×(T2 intensity), wherein steps (a) and (b) can be performed in any order, and (c) selecting an optical value, as the predetermined cut off, which optical value is (i) in excess of every one of the calculated optical values for each of the plurality of samples in step (a) which do not contain CSF, and (ii) is below every one of the calculated optical values for each of the plurality of samples in step (b) which do contain CSF, so as to determine the predetermined cutoff value.

15. A lateral flow device for detecting the presence of cerebrospinal fluid in a liquid biological sample, the device comprising, in sequential order for lateral flow of a liquid, a sample pad; a conjugate pad; a binding portion; and an absorbent pad;
wherein
a) the sample pad comprises a portion suitable to allow liquid sample flow;
b) the conjugate pad comprises both (A) and (B), wherein
   (A) comprises first plurality of transferrin-binding antibodies conjugated to a first plurality of nanoparticles, and
   (B) comprises a plurality of lectin molecules conjugated to a second plurality of nanoparticles, which nanoparticles are free to move laterally along the device when a liquid is present thereon;
c) the binding portion comprises the following separate domains:
   a. a domain which comprises a second plurality of transferrin-binding antibodies which are adhered to the surface of the lateral flow device; and
   b. a dried blood serum reagent domain adhered to the surface of the lateral flow device.

16. The device of claim 15, wherein a dried blood serum reagent has been diluted 90× to 100× prior to being adhered to the surface of the lateral flow device.

17. A kit comprising:
the lateral flow device recited in claim 1; and
ii) a diluent buffer for diluting a clinical liquid sample from a patient.

18. A method comprising:
performing surgery on the central nervous system and/or meninges of a subject;
obtaining one or more samples of the subject's blood or serum or other biological liquid, wherein if more than one sample is obtained then the samples are obtained at different time points during the surgery; and
detecting if cerebrospinal fluid (CSF) has leaked into the blood or serum or other biological liquid of the subject during surgery comprising the method of claim 1, on the sample(s) obtained, wherein the biological liquid is not CSF itself.

19. The method claim 18, wherein the sample is a serum sample, an otorrhea sample, a rhinorrhea sample, or comprises drainage from a spinal suture area.

20. A method of diagnosing a subject as having a cerebrospinal fluid leak comprising:
detecting if cerebrospinal fluid (CSF) is present in a biological liquid sample from the subject, which is not CSF itself, comprising using the device of claim 15, and,
where CSF has been detected as present in the sample, diagnosing the subject as having a cerebrospinal fluid leak.

* * * * *